(12) United States Patent
Pechacek et al.

(10) Patent No.: US 6,262,305 B1
(45) Date of Patent: Jul. 17, 2001

(54) PROCESS AND INTERMEDIATES FOR PREPARING 3-(SUBSTITUTED PHENYL)-5-(THIENYL OR FURYL)-1,2,4-TRIAZOLE COMPOUNDS

(75) Inventors: James T. Pechacek, Indianapolis; Francis E. Tisdell, Carmel, both of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/389,702

(22) Filed: Sep. 3, 1999

Related U.S. Application Data

(62) Division of application No. 09/048,601, filed on Mar. 26, 1998, now Pat. No. 6,015,826.
(60) Provisional application No. 60/044,697, filed on Apr. 24, 1997, and provisional application No. 60/066,135, filed on Nov. 19, 1997.
(51) Int. Cl.$^7$ .................................................. C07C 327/58
(52) U.S. Cl. ............................................................. 564/248
(58) Field of Search ............................................. 564/248

(56) References Cited

U.S. PATENT DOCUMENTS

| | | | |
|---|---|---|---|
| 4,038,405 | 7/1977 | Evans et al. | 424/269 |
| 5,284,860 | 2/1994 | Ozaki et al. | 514/340 |
| 5,318,959 | 6/1994 | Ozaki et al. | 514/63 |
| 5,380,944 | 1/1995 | Ozaki et al. | 564/81 |
| 5,466,705 | 11/1995 | Ozaki et al. | 514/383 |
| 5,482,951 | 1/1996 | Ozaki et al. | 514/340 |
| 5,567,825 | 10/1996 | Ohi et al. | 548/264.2 |
| 5,616,594 | 4/1997 | Ozaki et al. | 515/340 |

FOREIGN PATENT DOCUMENTS

| | | |
|---|---|---|
| 0 572 142 | 12/1993 | (EP) . |
| 0 648 752 | 4/1995 | (EP) . |
| 1039459 | * 8/1966 | (GB) . |
| 5-310712A | 11/1993 | (JP) . |
| 7-33731A | 2/1995 | (JP) . |
| 7-76577A | 3/1995 | (JP) . |
| 8-12657A | 1/1996 | (JP) . |
| 8-92224 | 4/1996 | (JP) . |
| 8-245315A | 9/1996 | (JP) . |
| 8-283261A | 10/1996 | (JP) . |
| WO94/24110 | 10/1994 | (WO) . |
| WO95/33732 | 12/1995 | (WO) . |
| WO9847894 | 10/1998 | (WO) . |

OTHER PUBLICATIONS

S. Ito et al., "N–Methyl–N–(phenylsulfonyl)benzo hydrazonoyl chloride as a potential intermediate for nitrogen–heterocycles. Preparation of 1–methyl–3–phenyl–1H–1,2, 4–triazoles and –pyrazoles," Bulletin of the Chemical Society of Japan, vol. 56, No. 2, Feb. 1983, pp 545–58.
Derwent Abstract 96–074864/08, abstracting JP 7330742–A (1996).
Derwent Abstract 95–151828/20, abstracting JP 07076577A (1965).
Derwent Abstract 96–236057/24, abstracting JP 8092224A (1996).
Derwent Abstract 96–087618/09, abstracting EP 717039A (1996).
Derwent Abstract 96–350182/35, abstracting JP 8165283A (1996).
Derwent Abstract 96–482063/48, abstracting JP 8245315A (1996).
Derwent Abstract 97–017357/02, abstracting JP 08283261A (1997).

* cited by examiner

*Primary Examiner*—Patricia L. Morris
(74) *Attorney, Agent, or Firm*—Donald R. Stuart; Craig E. Mixan

(57) ABSTRACT 3-(Substituted phenyl)-5-(thienyl or furyl)-1,2,4-triazole compounds are useful as insecticides and acaricides. New synthetic procedures and intermediates for preparing the compounds, pesticide compositions containing the compounds, and methods of controlling insects and mites using the compounds are also provided.

1 Claim, No Drawings

PROCESS AND INTERMEDIATES FOR PREPARING 3-(SUBSTITUTED PHENYL)-5-(THIENYL OR FURYL)-1,2,4-TRIAZOLE COMPOUNDS

RELATED APPLICATIONS

This application is a Divisional of prior application No. 09/048,601, filed Mar. 26, 1998, now U.S. Pat. No. 6,015,826, which claims the priority of U.S. patent application Ser. No. 60/044,697, filed Apr. 24, 1997, and Ser. No. 60/066,135, filed Nov. 19, 1997.

FIELD OF THE INVENTION

This invention provides new compounds that are useful as insecticides and acaricides, new synthetic procedures and intermediates for preparing the compounds, pesticide compositions containing the compounds, and methods of controlling insects and mites using the compounds.

BACKGROUND OF THE INVENTION

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

A number of 3,5-diphenyl-1H-1,2,4-triazole derivatives have been described in the literature as having acaricidal activity. U.S. Pat. No. 5,482,951; JP 8092224, EP572142, JP 08283261. To applicants knowledge, however, none of these compounds has become a commercial product. Nitro furanyl triazoles are described by L. E. Benjamin and H. R. Snyder as antimicrobials (*J. Heterocyclic Chem.* 1976, 13, 1115) and by others as antibacterials (*J. Med. Chem.* 1973, 16(4), 312–319; *J. Med. Chem.* 1974, 17(7), 756–758). The present invention provides novel compounds with commercial level activity against mites and insects.

SUMMARY OF THE INVENTION

This invention provides novel substituted thienyl and furanyl triazole derivatives especially useful for the control of insects and mites.

More specifically, the invention provides novel insecticidally active compounds of the formula (1)

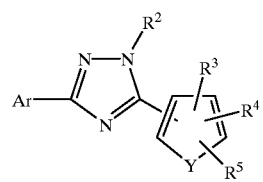

(1)

wherein

Ar is substituted phenyl;

Y is O or S;

$R^2$ is lower alkyl, haloalkyl, lower alkenyl, lower alkynyl, or alkoxyalkyl;

$R^3$ is selected from H, halo, lower alkyl, $(C_7-C_{21})$ straight or branched chain alkyl, hydroxy, lower alkoxy, haloalkyl, haloalkoxy, alkoxyalkyl, alkoxyalkoxy, lower alkenyl, lower alkynyl, haloalkenyl, CN, $NO_2$, $COR^6$, $CO_2R^6$, $CON(R^6)_2$, $(C_3-C_6)$ cycloalkyl, $S(O)_m R^6$, $-OSO_2R^6$, SCN, $-(CH_2)_n R^6$, $-CH=CHR^6$, $-C\equiv CR^6$, $-(CH_2)_q OR^6$, $(CH_2)_q SR^6$, $-(CH_2)_q NR^6R^6$, $O(CH_2)_q R^6$, $-S(CH_2)_q R^6$, $-NR^6(CH_2)_q R^6$,

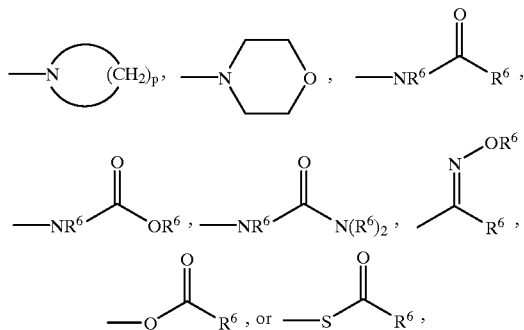

$-Si(R^7)_3$ pyridyl, substituted pyridyl, isoxazolyl, substituted isoxazolyl, naphthyl, substituted naphthyl, phenyl, substituted phenyl, thienyl, substituted thienyl, pyrimidyl, substituted pyrimidyl, pyrazolyl, or substituted pyrazolyl;

$R^4$ and $R^5$ are independently H, halo, lower alkyl, lower alkoxy, haloalkyl, haloalkoxy, CN, $CO_2R^6$, $CON(R^6)_2$, or $S(O)_m$ alkyl, or if $R^4$ and $R^5$ are attached to adjacent carbon atoms, they may join to form a 5 or 6 member saturated or unsaturated carbocyclic ring which may be substituted by 1 or 2 halo, lower alkyl, lower alkoxy or haloalkyl groups;

$R^6$ is H, lower alkyl, haloalkyl, lower alkenyl, lower alkynyl, phenyl, or substituted phenyl;

$R^7$ is lower alkyl;

m is 0, 1, or 2;

n is 1 or 2;

p is an integer from 2 to 6; and q is 0 or 1;

or a phytologically acceptable acid addition salt thereof.

A preferred group of compounds are those of formula (1A)

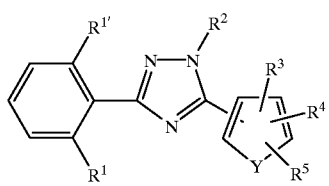

(1A)

wherein $R^1$ and $R^{1'}$ are independently H, Cl, F, methyl, halomethyl, methoxy, or halomethoxy;

Y is O or S;

$R^2$ is lower alkyl, haloalkyl, lower alkenyl, lower alkynyl, or alkoxyalkyl;

$R^3$ is selected from H, halo, lower alkyl, $(C_7-C_{21})$ straight chain alkyl, hydroxy, lower alkoxy, haloalkyl, haloalkoxy, alkoxyalkyl, alkoxyalkoxy, lower alkenyl, haloalkenyl, CN, NO$_2$, CO$_2$R$^6$, CON(R$^6$)$_2$, (C$_3$–C$_6$) cycloalkyl, S(O)$_m$R$^6$, SCN, pyridyl, substituted pyridyl, isoxazolyl, substituted isoxazolyl, naphthyl, substituted naphthyl, phenyl, substituted phenyl, —(CH$_2$) R$^6$, —CH=CHR$^6$, —C≡CR$^6$, —CH$_2$OR$^6$, —CH$_2$NR$^6$R$^6$, —OCH$_2$R$^6$, —SCH$_2$R$^6$, —NR$^6$CH$_2$R$^6$,

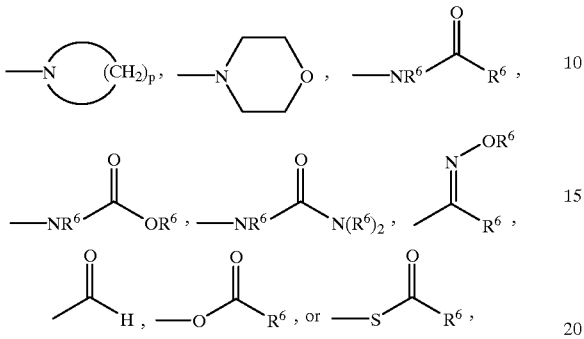

R$^4$ and R$^5$ are independently H, halo, lower alkyl, lower alkoxy, haloalkyl, haloalkoxy, CN, CO$_2$R$^6$, CON(R$^6$)$_2$, or S(O)$_m$ alkyl, or R$^4$ and R$^5$ form a 5 or 6 member saturated or unsaturated carbocyclic ring which may be substituted by 1 or 2 halo, lower alkyl, lower alkoxy or haloalkyl groups;

R$^6$ is H, lower alkyl, haloalkyl, lower alkenyl, lower alkynyl, phenyl, or substituted phenyl;

m is 0, 1, or 2; and n is 1 or 2;

p is an integer from 2 to 6;

or a phytologically acceptable acid addition salt thereof.

Preferred compounds of formula (1A) include the following classes:

a) compounds of formula (1A) wherein R$^{1'}$ is F;
b) compounds of formula (1A) wherein Y is sulfur;
c) compounds of formula (1A), and particularly compounds of the foregoing classes a) and b), wherein R$^1$ and R$^{1'}$ are independently Cl or F;
d) compounds of formula (1A), and particularly compounds of the foregoing classes a) through c) wherein R$^1$ and R$^{1'}$ are both F;
e) compounds of formula (1A), and particularly compounds of the foregoing classes a) through c) wherein R$^1$ and R$^{1'}$ are both Cl;
f) compounds of formula (1A), and particularly compounds of the foregoing classes a) through c) wherein R$^1$ is Cl and R$^{1'}$ is F;
g) compounds of formula (1A), and particularly compounds of one of the foregoing classes a) through f) wherein R$^2$ is methyl;
h) compounds of formula (1A), and particularly compounds of one of the foregoing classes a) through g) wherein R$^3$, R$^4$, and R$^5$ are independently selected from H, halo, methyl, and methoxy;
i) compounds of formula (1A), and particularly compounds of one of the foregoing classes a) through g) wherein R$^3$, R$^4$, and R$^5$ are independently H or halo;
j) compounds of formula (1A), and particularly compounds of one of the foregoing classes a) through g) wherein R$^3$, R$^4$, and R$^5$ are independently H, Cl, or Br;
k) compounds of formula (1A), an particularly compounds of one of the foregoing classes a) through g) wherein R$^3$, R$^4$, and R$^5$ are each halo;
l) compounds of formula (1A), and particularly compounds of one of the foregoing classes a) through g) wherein R$^3$, R$^4$, and R$^5$ are each chloro.

A particularly preferred class of compounds includes those of formula (1B)

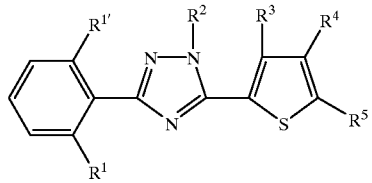

wherein

R$^1$ and R$^{1'}$ are independently F or Cl;

R$^2$ is lower alkyl, with methyl being most preferred; and

R$^3$, R$^4$ and R$^5$ are independently H, Cl, or Br.

The invention also provides new processes and intermediates for preparing compounds of formula (1) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The term "lower alkyl" refers to (C$_1$–C$_6$) straight hydrocarbon chains and (C$_3$–C$_6$) branched and cyclic hydrocarbon groups.

The terms "lower alkenyl" and "lower alkynyl" refer to (C$_2$–C$_6$) straight hydrocarbon chains and (C$_3$–C$_6$) branched hydrocarbon groups containing at least one double or triple bond, respectively.

The term "lower alkoxy" refers to -O-lower alkyl.

The terms "halomethyl" and "haloalkyl" refer to methoxy and lower alkyl groups substituted with one or more halo atoms.

The terms "halomethoxy" and "haloalkoxy" refer to methyl and lower alkoxy groups substituted with one or more halo atoms.

The term "alkoxyalkyl" refers to a lower alkyl group substituted with a lower alkoxy group.

The terms "substituted naphthyl", "substituted thienyl," "substituted pyrimidyl," "substituted pyrazolyl," "substituted pyridyl," and "substituted isoxaxolyl" refer to the ring system substituted with one or more groups independently selected from halo, halo (C$_1$–C$_4$) alkyl, CN, NO$_2$, (C$_1$–C$_4$) alkyl, (C$_3$–C$_4$) branched alkyl, phenyl, (C$_1$–C$_4$) alkoxy, or halo (C$_1$–C$_4$) alkoxy.

The term "substituted phenyl" refers to a phenyl group substituted with one or more groups independently selected from halo, (C$_1$–C$_{10}$) alkyl, branched (C$_3$–C$_6$) alkyl, halo (C$_1$–C$_7$) alkyl, hydroxy (C$_1$–C$_7$) alkyl, (C$_1$–C$_7$) alkoxy, halo (C$_1$–C$_7$) alkoxy, phenoxy, phenyl, NO$_2$, OH, CN, (C$_1$–C$_4$) alkanoyl, benzoyl, (C$_1$–C$_4$) alkanoyloxy, (C$_1$–C$_4$) alkoxycarbonyl, phenoxycarbonyl, or benzoyloxy.

The term "substituted benzenesulfonyl" refers to p-chlorobenzenesulfonyl and p-toluenesulfonyl.

Unless otherwise indicated, when it is stated that a group may be substituted with one or more substituents selected from an identified class, it is intended that the substituents may be independently selected from the class.

Synthesis

Compounds of formula (1) can be prepared by the methods described in U.S. Pat. Nos. 5,380,944 and 5,284,860 (Production Methods 1, 2 and 3). Additional methods will be described hereinafter.

For example, compounds of Formula (1) wherein $R^{1'}$ is F can be prepared in accordance with the following reaction Scheme I:

Scheme I

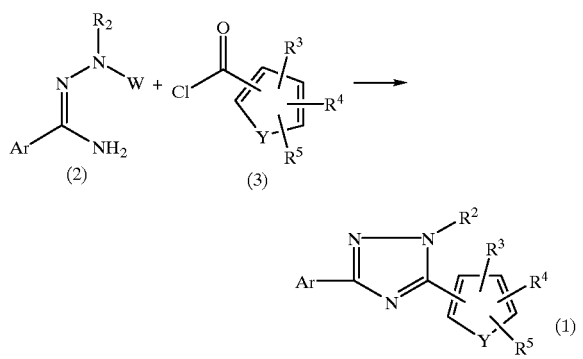

wherein Ar, $R^2$, $R^3$, $R^4$, $R^5$ and Y are as defined in formula (1), and W is a conventional amino protecting group. Examples of conventional amino protecting groups include, but are not limited to, the carbobenzyloxy group, tertiary alkoxycarbonyl groups, amides, phosphinyl and phosphoryl groups, and sulfenyl and sulfonyl groups. As illustrated in Scheme I, an N-protected amidrazone (2) is reacted with a compound of formula (3) in the presence of acid or base as catalyst. Intermediates of formulas (2) and (3) may be obtained by application of well known procedures.

An example of an intermediate of formula (3) is 3,4,5-trichlorothiophene-2-carboxylic acid chloride. The carboxylic acid can be obtained by the treatment of tetrachlorothiophene with n-butyllithium and subsequent quenching with carbon dioxide as in *J.Organometal.* 1968, 13, 419–430. Conversion of carboxylic acid to the acid chloride is carried out by conventional methods, as illustrated hereinafter in Example 2.

Scheme II illustrates preparation of the protected benzamidrazone starting material (2).

Scheme II

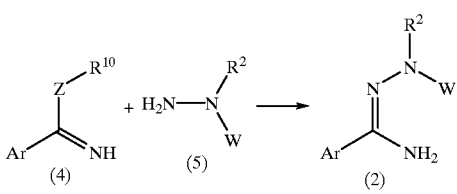

Benzimidate derivative (4), wherein Z is C or S, and $R^{10}$ is lower alkyl, is reacted with hydrazine derivative (5), wherein Ar, W, and $R^2$ are as defined above for Scheme I.

An example of an intermediate of formula (5) is N-methyl-N-t-butylcarboxyhydrazine. Its use in making regiospecific 1-alkyl [1,2,4] triazoles is found in *Chem. Ber.* 1982, 115, 2807–2818. The production of benzimide compounds is well known. An example is disclosed in *Synth. Commun.* 1983, 13, 753.

Another aspect of the invention is a new method for preparing compounds of formula (1A) wherein $R^1$ and $R^{1'}$ are F, as illustrated in Scheme III:

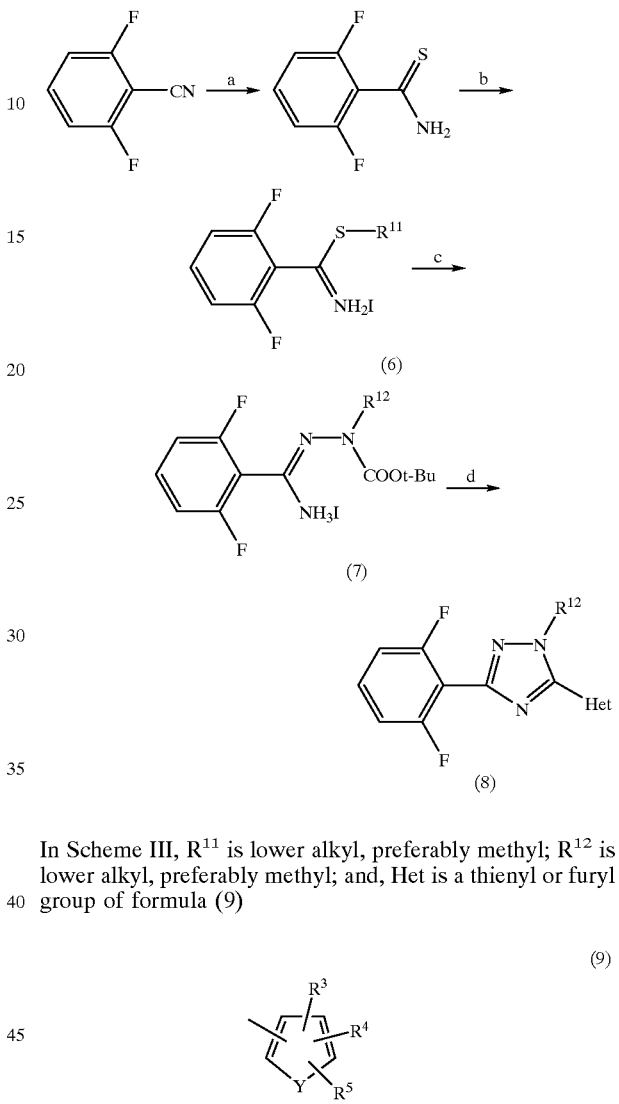

In Scheme III, $R^{11}$ is lower alkyl, preferably methyl; $R^{12}$ is lower alkyl, preferably methyl; and, Het is a thienyl or furyl group of formula (9)

where Y, $R^3$, $R^4$, and R5 are as defined in formula (1). The process illustrated in Scheme III is also applicable to preparation of compounds wherein Het is any of a variety of other heterocyclic groups, for example pyridyl and pyrazolyl.

In another of its aspects, the invention provides novel intermediates of the formulas (6) and (7), as defined above.

As illustrated in step a of Scheme III, 2,6-difluorobenzonitrile is reacted with triethylamine, sodium sulfide hydrate, and hydrochloric acid in pyridine at room temperature to give 2,6-difluorobenzenethioamide.

In step b of Scheme III the 2,6-difluorobenzenethioamide is reacted with lower alkyl iodide, e.g. iodomethane, in acetone to provide an S-(lower alkyl)thio-2,6-difluorobenzimidinium iodide of formula (6). Acetone is the preferred solvent, however other polar aprotic solvents such as DMF or THF can be used.

In step c of Scheme III the S-(lower alkyl)thio-2,6-difluorobenzimidinium iodide is reacted with an N-t-butoxycarbonyl-N-(lower alkyl)hydrazine to provide the amidrazone of formula (7). The reaction is carried out in methanol or ethanol, preferably methanol, at a temperature of 0° C. to the boiling point of the solvent.

In step d of Scheme III, the amidrazone of formula (7) is reacted with a thiophene or furan acid chloride in a nonreactive organic solvent such as benzene, toluene, xylenes, chloroform, dichloromethane, or 1,2-dichloroethane, at a temperature in the range from 0° C. to the boiling point of the solvent.

The process of Scheme III uses milder conditions than previously published processes, and therefore allows thermally sensitive heterocycles to be used. Higher yields are also provided.

A detailed illustration of steps a–c of Scheme III is given in Example 1 hereinafter. Detailed illustrations for step d are given in Examples 2–4 hereinafter.

EXAMPLE 1

The following steps illustrate preparation of the amidrazone of formula (2a)

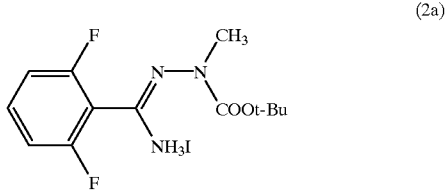

(2a)

A. 2,6-difluorobenzenethioamide.

Into a 3 L three necked round bottom flask equipped with a mechanical stirrer, dry ice condenser, dropping funnel, and outlet to a trap filled with bleach was added pyridine (550 mL), 2,6-difluorobenzonitrile (208 g, 1.50 mol), triethylamine (202 g, 279 mL, 2.0 mol), and sodium sulfide hydrate (521 g, 2.17 mol-broken into pieces small enough to fit into the flask). The temperature of the stirred mixture was lowered to approximately 5° C. and to the slurry was added dropwise concentrated hydrochloric acid (143 g, 288 mL, 3.99 mol). An exotherm was noted and the rate of addition of the hydrochloric acid was such that the temperature of the reaction mixture did not exceed 25° C. for a total addition time of 75 min. The cooling bath was removed and the slurry was allowed to warm to RT and to stir over night. The mixture was poured into water (2 L) and was extracted with ether (3×500 mL). The ether layer was washed with dilute sulfuric acid, water, brine, dried (MgSO$_4$), and the solvent removed in vacuo to give 232 grams of crude product. The starting material was removed from the product via kugelrohr distillation to give 197 g (76%) of 2,6-difluorobenzenethioamide. This material was used without further purification.

B. S-methylthio-2,6-difluorobenzainidinium iodide

Into a 3 L three necked flask equipped with a mechanical stirrer and dropping funnel was added acetone (1150 mL) and 2,6-difluorobenzenethioamide (197 g, 1.14 mol). The temperature of the stirred solution was lowered to approximately 5° C. and iodomethane (161 g, 70.6 mL, 1.14 mol) was added dropwise. The ice bath was removed and the slurry was allowed to stir over night. The resulting yellow solids were removed via filtration and washed with ether to obtain 223 grams. An additional portion of material was obtained from the filtrate by removal of the solvent in vacuo. Ether was added to the residue and the resulting solids removed via filtration to obtain an additional 57 grams of material. The combined solids totaled 280 g (77.9% yield) of S-methylthio-2,6-difluoro-benzimidinium iodide: mp 168–169° C.; $^1$H NMR (DMSO-d$_6$) δ 7.7 (m, 1H), 7.4 (m, 2H), 2.7 (s, 3H)

C. N-tert-butoxycarbonyl-N-methylhydrazine

Into a 1 L three necked round bottom flask equipped with a mechanical stirrer and dropping funnel was added methyl hydrazine (42.2 g, 0.916 mol) and THF (100 mL). The temperature of the mixture was cooled to 5° C. and a solution of di-tert-butyl dicarbonate (100 g, 0.458 mol) dissolved in THF (150 mL) was added dropwise. The cooling bath was removed and the mixture was stirred at RT overnight. The liquid was decanted from a gummy precipitate and the solvent removed in vacuo to give approximately 70 grams of a clear liquid. The gummy precipitate was partitioned between methylene chloride and water. The methylene chloride was washed with brine, dried (Na$_2$SO$_4$) and the solvent removed in vacua. The resulting residue was combined with that from the previous evaporation and distilled at approximately 20 mm Hg (bp 77–78° C.) to give 40.2 g (60% yield) of N-tert-butoxycarbonyl-N-methylhydrazine: $^1$H NMR (CDCl$_3$) δ 4.1 (s, b, 2H), 3.05 (s, 3H), 1.5 (s, 9H)

D. Amidrazone of formula (2a)

Into a 1 L round bottom flask equipped with a mechanical stirrer, dropping funnel, and outlet to a trap filled with bleach, was added S-methyl-2,6-difluorobenziminium iodide (63.8 g, 0.202 mol) and methanol (180 mL). To the stirred solution was added dropwise N-tert-butoxycarbonyl-N-methylhydrazine (29.6 g. 0.202 mol). The solution was allowed to stir overnight and the methanol was removed in vacuo. The residue was triturated with ether and the solids removed via filtration to give 66.3 grams (79.0% yield) of the amidrazone of formula (2a): mp 172–173° C. (dec); H NMR (DMSO-d$_6$) δ 12.3 (s, b, 1H), 10.4 (d, b, 2H), 7.9 (m, 1H), 7.4 (m, 2H), 3.1 (s, 3H), 1.5 (s, 9H).

EXAMPLE 2

3-(2,6-difluorophenyl)-5-(3-n-hexylthien-2-yl)-1-methyl[1,2,4]triazole (Compound 35)

To a mixture of 3-n-hexyl-2-thiophene carboxylic acid (0.5 g, 2.4 mmol) in 25 mL of dry 1,2-dichloroethane was added 2.0 mL of thionyl chloride and a drop of dimethylformamide. The mixture was refluxed for four hours. After cooling, the reaction mixture was evaporated in vacuo and the residue was combined with 25 mL of dry toluene and 1.24 g (3.0 mmol) of the amidrazone of formula (2a) (Example 1). The mixture was refluxed overnight, cooled, and then partitioned between brine and ether. The organic phase was dried (MgSO$_4$), the solvent evaporated, and the residue was chromatographed on silica gel using ethyl acetate/hexanes as the eluant; 5:95 to 20:80. The product fractions were collected and evaporated to give 0.66 g (76% yield) of the title product as an oil. $^1$H NMR δ 7.26–7.46 (m, 2H), 6.97–7.06 (m, 2H), 3.97 (s, 3H) 2.71 (m, 2H), 1.23 (m, 6H), 0.84 (m, 3H); calcd. for C$_{19}$H$_{21}$F$_2$N$_3$S: C, 63.14; H, 5.86; N, 11.63; S, 8.87; Found: C,62.90 ; H. 5.79; N, 11.70; S, 8.77.

EXAMPLE 3

3-(2,6-difluorophenyl)-5-(4-p-chlorobenzenesulfonyl-3-methylthien-2-yl)-1-methyl[2,4]triazole (Compound 12)

To a solution of 0.9 g (2.2 mmol) of the amidrazone of formula (2a)(Example 1) and 0.75 g (2.2 mmol) of the thiophene acid chloride, 4-(p-chlorobenzenesulfonyl)-3- methylthiophene-2-carbonyl chloride, in 100 mL of toluene was added 1 equivalent (0.4 g, 2.2 mmol) p-toluenesulfonic acid monohydrate with stirring. The mixture was refluxed overnight using a Dean-Stark trap to remove water. The solution was cooled and the solvent removed in vacuo. The residue was dissolved in 100 mL of dichloromethane and was washed with 2N NaOH and then with water. The organic phase was dried (MgSO$_4$) and the solvent evaporated. The residue was recrystallized from ethyl acetate/hexanes to give 0.6 g of the product as off-white crystals. mp 183–185° C. 59.4% yield. $^1$H NMR δ 8.4 (s, 1H), 7.8 (d, 2H), 7.4 (d, 2H) 7.3 (m, 1H), 7.0 (m, 2H), 3.98 (s, 3H), 2.25 (s, 3H); calcd. for $C_{20}H_{14}F_2ClN_3O_2S_2$: C, 51.55; H, 3.01; N, 9.02; Found: C,51.76 ; H, 3.26; N, 8.92.

EXAMPLE 4

3-(2,6-difluorophenyl)-5-(5-p-chlorophenyl)furan-2-yl)-1-methyl[1,2,4]triazole (Compound 13)

To a solution of 1.0 g (2.4 mmol) of the amidrazone of formula (2a) (Example 1) and 0.61 g (2.4 mmol) of 5-[p-chlorophenyl]-furan-2-carbonyl chloride in 100 mL of toluene was added 1 equivalent (0.43 g, 2.4 mmol) p-toluenesulfonic acid monohydrate with stirring. The mixture was refluxed overnight using a Dean-Stark trap to remove water. The solution was cooled and the solvent removed in vacuo. The residue was dissolved in 100 mL of dichloromethane and was washed with 2N NaOH and then with water. The organic phase was dried (MgSO$_4$) and the solvent evaporated. The residue was recrystallized from ethyl acetate/hexanes to give 0.4 g of the product as off white crystals mp 171–173° C. 44.9% yield; calcd. for $C_{19}H_{12}F_2ClN_3O$: C, 61.37; H, 3.23; N, 11.30; Found: C,61.34 ; H, 3.19; N, 11.06.

The invention also provides a new method for preparing compounds of formula (1A) as illustrated in Scheme IV:

Scheme IV

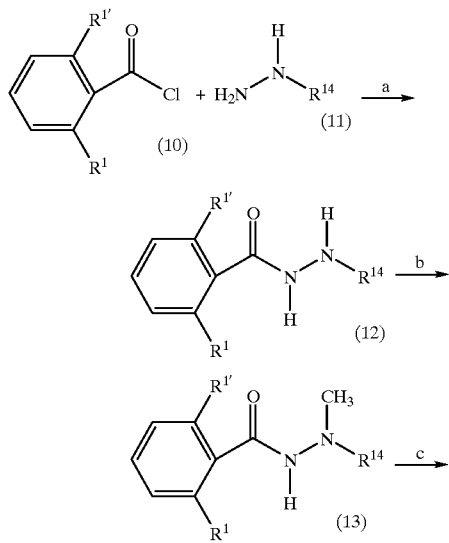

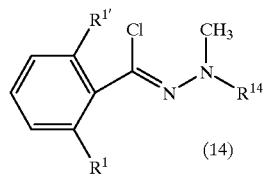

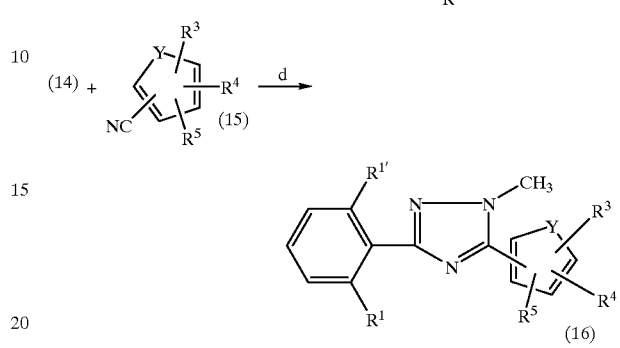

wherein R$^1$, R$^{1'}$, Y, R$^3$, R$^4$, and R$^5$ are as defined in formula (1) and R$^{14}$ is methanesulfonyl, benzenesulfonyl, or substituted benzenesulfonyl.

In step a, 2,6-substitutedbenzoylchloride (10) is reacted with a hydrazide of formula (11) (wherein R$^{14}$ is methanesulfonyl, benzenesulfonyl, or substituted benzenesulfonyl, i.e. p-Cl or p-CH$_3$ benzenesulfonyl) and triethylamine in THF to give the substituted benzhydrazone of formula (12).

In step b, the substitued benzhydrazone of formula (12) is reacted first with sodium hydride in N,N-dimethylformamide and then with iodomethane to produce the substituted hydrazine of formula (13).

In step c the substituted hydrazine of formula (13) is chlorinated using, e.g. PCl$_5$ to produce substituted benzylhydrazonoyl chloride of formula (14). The reaction is carried out in a non-reactive organic solvent such as dichloroethane.

In step d the substituted benzylhydrazonoyl chloride of formula (14) is reacted with a mixture of aluminum chloride and cyanothiophene or cyanofuran of formula (15) in a solvent, e.g. o-dichlorobenzene, to produce a 3-(2,6-substituted phenyl)-5-(substituted thienyl)-1-methyl[1,2,4] triazole of formula (16).

A detailed illustration of steps a–c of Scheme IV is given in Example 5 hereinafter. Detailed illustrations of step d are given in Examples 6–9, 11, 13, and 15 hereinafter.

EXAMPLE 5

The following steps show preparation of the benzhyrazonoyl chloride of formula (14a)

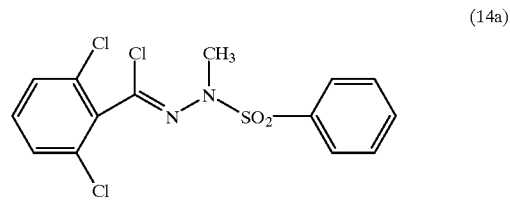

A. 1-Benzenesulfonyl-2-(2,6-dichloro)benzhydrazone

Into a 1 L three necked round bottom flask equipped with a condenser, mechanical stirrer, thermometer, under an atmosphere of nitrogen, was added THF (500 mL), benzenesulfonyl hydrazide (41.1 g, 0.238 mol), and triethylamind (24.1 g, 33.2 mL, 0.238 mol). The resulting solution was cooled to −5° C. and 2,6-dichlorobenzoyl chloride (50.0 g, 34.2 mL, 0.238 mol) was added dropwise over a 55-min period and the temperature did not rise above 0° C. The reaction mixture was allowed to stir for 1 hr and then the cooling bath was removed and the reaction mixture was then stirred 21 hr at room temperature with monitoring via TLC and HPLC. Most of the solvent was removed in vacuo and the residue partitioned between methylene chloride (1000 mL) and water (2×200 mL). The organic layer was washed with saturated brine (250 mL), dried ($Na_2SO_4$), and the solvent removed in vacuo to give a white solid. The white solids were slurried in ether and were removed via filtration and dried in vacuo overnight to give 74.3 g (90.5% yield of 1-benzenesulfonyl-2-(2,6-dichlorobenz)hydrazone: mp 180–181° C.; TIC mass 345/347/349; $^1$H NMR (CDCl$_3$) δ 8.05 (m, 2H), 7.9 (m, 1H), 7.5–7.7 (m, 4H), 7.3 (m, 3H).

B. 1-(2,6-dichloro)benzoyl-2-methyl-2-benzenesulfonyl hydrazine

In a 1 L three necked round bottom flask equipped with a mechanical stirrer, thermometer, and dropping funnel under an atmosphere of nitrogen a suspension of sodium hydride (8.49 g of 60% dispersion, 0.212 mol) was washed with hexanes (3 portions) and most of the hexane from the final wash was removed via suction. N,N-dimethylformamide (200 mL) was added and the temperature of the slurry lowered to −5° C. A solution of N-benzenesulfonyl-2,6-dichloro-benzhydrazone (73.3 g, 0.212 mol, in 300 mL of N,N-dimethylformamide) was added dropwise over a 120 min period at a rate such that the temperature did not rise above 3° C. and the rate of hydrogen evolution was maintained at a manageable rate. As the addition proceeded the mixture turned lemon yellow and thickened, but when the addition was completed the mixture was clear and easily stirred. The resulting mixture was stirred at 0° C. for 1 hr and the cooling bath removed and stirred for an additional 1 hr (temperature rose to 15° C.). The mixture was then cooled to −5° C. and iodomethane (30.0 g, 13.2 mL) was added dropwise at a rate such that the temperature did not rise above 0° C. The cooling bath was removed and the reaction mixture was allowed to warm to room temperature and to stir for 2 hr. The reaction mixture was diluted with brine (300 mL) and extracted with ethyl acetate. The organic layer was washed with saturated brine, dried ($Na_2SO_4$), and the solvent removed in vacuo to give crude material contaminated with N,N-dimethylformamide which was removed via vacuum pump. The crude mixture was crystallized in hexanes/ethyl acetate, the solids removed via filtration, and dried in vacuo to give 40.2 g. Solvent was removed from the filtrate to obtain an additional 21.4 g for a total of (80.9% yield) of 1-(2,6-dichlorobenzoyl)-2-methyl-2-benzenesulfonyl hydrazine: mp 177–178° C.; $^1$H NMR (CDCl$_3$) δ 8.0 (m, 2H), 7.4–7.8 (m, 4H), 7.2 (m, 3H), 3.4 and 3.05 (two singlets combined for 3H).

C. N-(Benzenesulfonyl)-N-methyl-(2,6-dichlorobenz) hydrazonoyl chloride

Into a 1 L three necked round bottom flask equipped with a magnetic stirrer and condenser under an atmosphere of nitrogen was added N-benzenesulfonyl-N-methyl-2,6-dichlorobenzoyl hydrazine (35.9 g, 0.10 mol), 1,2-dichloroethane (500 mL), and phosphorus pentachloride (31.2 g, 0.15 mol). The temperature of the mixture was raised to the point of reflux and was allowed to stir for 30 min. The solvent was removed in vacuo and the residue dissolved in methylene chloride and carefully diluted with water. The organic phase was washed with water, brine, dried ($Na_2SO_4$) and the solvent removed in vacuo to give an oil which solidified when triturated with ethyl acetate/hexanes mixture to give 36.1 g (95.7% yield) N-benzenesulfonyl-N-methyl-2,6-dichlorobenzhydrazonoyl chloride as a white crystalline solid: mp 103–104° C.; $^1$H NMR (CDCl$_3$) δ 7.9 (m, 2H), 7.4–7.7 (m, 3H), 7.2–7.4 (m, 3H), 3.1 (s, 3H)

N-Benzenesulfonyl-N-methyl-2-chloro-6-fluorobenzhydrazonoyl chloride was also made using the same procedure.

EXAMPLE 6

3-(2-chloro-6-fluorophenyl)-5-(3,4,5-trichlorothien-2-yl)-1-methyl[1,2,4]triazole (Compound 2)

To a mixture of N-methyl-N-benzenesulfonyl-2-chloro-6-fluorobenzhydrazonoyl chloride (47.5 g, 0.131 mol) and 2-cyano-3,4,5-trichlorothiophene (26.5 g 0.125 mol in o-dichlorobenzene (18 mL),was added aluminum chloride (11.1 g, 0.083 mol). The mixture was lowered into a preheated oil bath maintained at 140–150° C. The mixture was allowed to remain in the hot oil bath 40 min and was then removed from the bath and stirred for 2 hr as it gradually cooled. The reaction mixture was poured into 2N sodium hydroxide (300 mL-enough to dissolve the aluminum salts) and extracted with methylene chloride (3×250 mL). The organic phases were combined, washed with brine, dried (MgSO$_4$), and the solvent removed in vacuo to give the crude product. The residue was placed on silica gel (150 g) and then chromatographed using ethyl acetate/hexanes as eluant to obtain 39.7 g (55.3% yield) of the title compound; 99.4% pure by GC analysis; mp 129–130° C.; $^1$H NMR (CDCl$_3$) δ 7.3 (m, 2H), 7.1 (m, 1H), 4.0 (s, 3H); Anal. for $C_{13}H_6Cl_4FN_3S$: Calcd. C, 39.32; H, 1.52; N, 10.58. Found C, 39.08; H, 1.30; N, 10.34.

EXAMPLE 7

3-(2,6-dichlorophenyl)-5-(3,4,5-trichlorothien-2-yl)-1-methyl[1,2,4]triazole (Compound 45)

Into a 500 mL round bottom flask equipped with a mechanical stirrer and condenser, under an atmosphere of nitrogen, was added o-dichlorobenzene (150 mL), 2-cyano-3,4,5-trichlorothiophene (23.6 g, 111 mmol), and aluminum chloride (14.8 g, 111 mmol). The stirred reaction mixture was plunged into an oil bath at 145–150° C. When the internal temperature of the mixture reached 133° C. N-(benzenesulfonyl)-N-methyl-(2,6-dichlorobenz) hydrazonoyl chloride (35.0 g, 92.6 mmol) was added in 5 gram portions over 40 min. The temperature rose to 141° C. The reaction mixture was allowed to stir from the initial addition of the N-(benzenesulfonyl)-N-methyl-(2,6-dichlorobenz)hydrazonoyl chloride 1 hr and 40 min with monitoring via HPLC and GC. The oil bath was dropped down from the reactor and the mixture was allowed to cool to approximately 90° C. and was added to stirred 2N caustic (350 mL). The mixture stirred for 5 min, was checked to insure that the pH was basic, and was diluted with methylene chloride (800 mL). The methylene chloride layer was washed with water (250 mL), brine (250 mL), dried ($Na_2SO_4$), the solvent removed in vacuo and the o-dichlorobenzene and benzenesulfonyl chloride were removed via kugelrohr distillation. The straw-colored solids were recrystallized from ethyl acetate to give 31.3 g (81.7% yield) of the title compound; mp 146–147° C.; $^1$H NMR (CDCl$_3$) δ 7.2–7.5 (m, 3H), 4.0 (s, 3H).

EXAMPLE 8

3-(2,6-dichlorophenyl)-5-(thien-3-yl)-1-methyl[1,2,4]triazole (Compound 48)

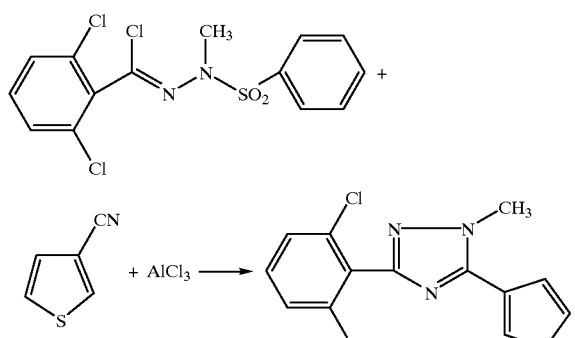

N-(Benzenesulfonyl)-N-methyl-(2,6-dichlorobenz)hyrazonoyl chloride (1.13 g, 3 mmol), 3-cyanothiophene (0.327 g, 6 mmol), and aluminum chloride (0.40 g, 3 mmol) were combined and heated at 135–140° C. for approximately 14 hours, and then stirred at room temperature for approximately 48 hours. The mixture was then diluted with dichloromethane, washed with water, washed with brine, and dried over magnesium sulfate. Chromatography produced 290 mg of the title product as a clear oil. $^1$H NMR (CDCl$_3$) δ 7.27–7.85 (m, 5H), 4.15 (s, 3H).

EXAMPLE 9

3-(2,6-dichlorophenyl)-5-(thien-2-yl)-1-methyl[1,2,4]triazole (Compound 50)

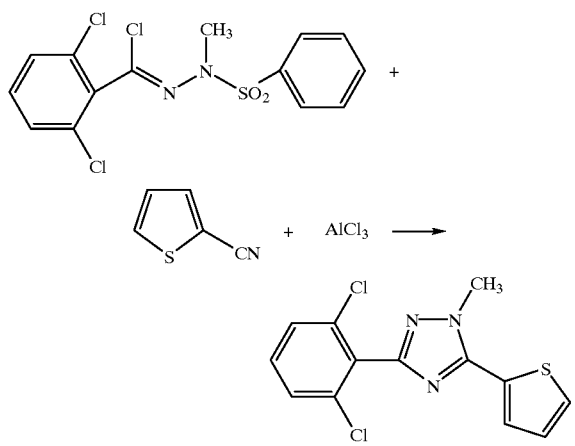

N-Benzenesulfonyl-N-methyl-2,6-dichlorobenzhyrazonoyl chloride (0.42 g, 1.1 mmol), 2-cyanothiophene (0.24g, 2.2 mmol), and aluminum chloride (0.147 g, 1.1 mmol) were combined and heated at 138° C. for approximately eight hours. The mixture was then poured into an ice bath of 1 M NaOH, and stirred one hour, extracted into dichloromethane, washed with brine, dried over magnesium sulfate and concentrated to 230 mg of an oil. Chromatography (SiO$_2$, 10% EtOAc-Hex) afforded the product (100 mg) as a white solid. MP 161–163° C.

The invention also provides the process for making compounds of formula (16) shown in Scheme V:

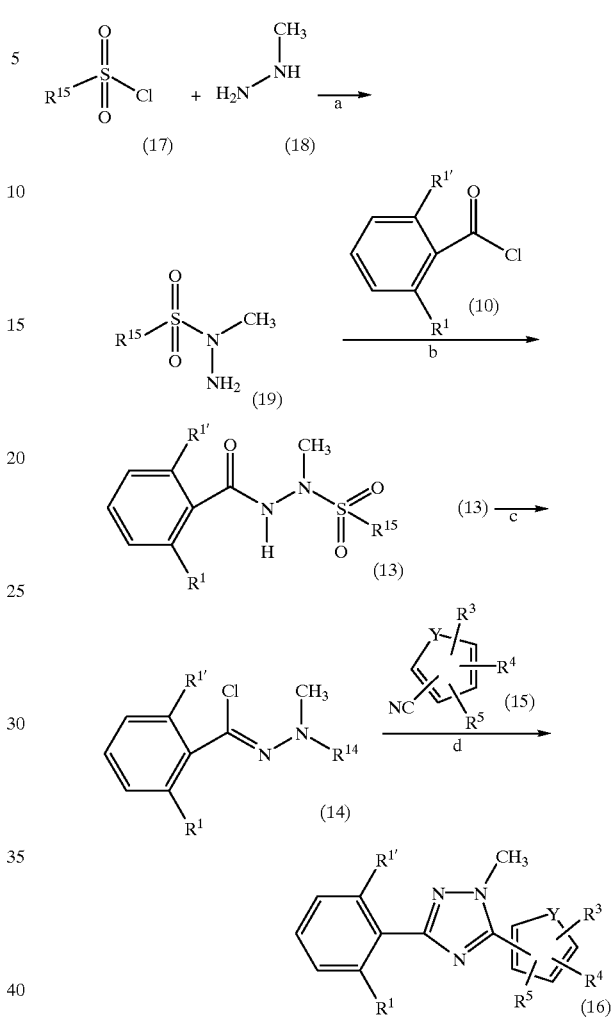

Scheme V wherein $R^{15}$ is methyl, phenyl, p-chlorophenyl, or p-tolyl, $R^{14}$ is methanesulfonyl, benzenesulfonyl, or substituted benzenesulfonyl, and $R^1_1$ $R^{11}$, $R^3_1$ $R^4_1$ and $R^5$ are as defined above for formula (1).

In step a of Scheme V, the sulfonyl chloride of formula (17) is reacted with methyl hydrazine in a nonreactive organic solvent such as THF in the presence of triethylamine. The reaction can be carried out at room temperature as is typically complete in four hours.

In step b of Scheme V, the sulfonyl hydrazine of formula (19) is reacted with the 2,6-substituted benzoyl chloride of formula (10) to provide the intermediate of formula (13).

Steps c and d of Scheme V are the same as steps c and d of Scheme IV.

EXAMPLE 10

This Example shows preparation of the benzhydrazonoyl chloride of formula (14b):

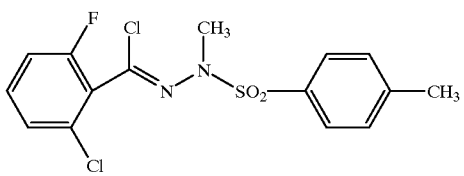

(14b)

A. 2-methyl-2-(4-methylphenyl)sulfonyl hydrazine

Into a 100 mL three necked round bottom flask equipped with a mechanical stirrer, thermometer, and dropping funnel under an atmosphere of nitrogen was added THF (25 mL), methylhydrazine (2.53 g, 2.92 mL, 55 mmol), and triethylamine (4.35 g, 5.99 mL, 55 mmol). The temperature of the mixture was lowered to approximately 5° C. and 4-methylbenzenesulfonyl chloride (9.5 g, 50 mmol) dissolved in 25 mL of THF was added dropwise at a rate such that the temperature did not rise over 10° C. The cooling bath was removed and the mixture was allowed to stir overnight at RT. Ether (100 mL) was added to the reaction mixture and the resulting slurry was washed with water (50 mL), brine (50 mL), dried ($Na_2SO_4$), and the solvent was removed in vacuo to give 9.5 g (95% yield) of the title product. $^1$H NMR ($CDCl_3$) δ 7.7 (d, 2H), 7.4 (d, 2H), 3.6 (s, b, 2H), 2.8 (s, 3H), 2.4 (s, 3H)

B. 1-(2-fluoro-6-chlorobenzoyl)-2-methyl-2-(4-methylphenyl)sulfonyl hydrazine

Into a 100 mL three necked round bottom flask equipped with a magnetic stirrer, thermometer, and condenser, under an atmosphere of nitrogen, was added 2-methyl-2-[(4-methylphenyl)sulfonyl] hydrazine (9.5 g, 47.4 mmol), pyridine (3.75 g, 3.83 mL, 47.4 mmol), 4-dimethylaminopyridine (0.30 g, 2.4 mmol) and acetonitrile (50 mL). The resulting mixture was cooled to 10° C. and 2-fluoro-6-chlorobenzoyl chloride (8.99 g, 45.2 mmol) dropwise at a rate such that the temperature did not rise above 10° C. The cooling bath was removed and the mixture was allowed to stir at RT overnight. The solvent was removed from the reaction mixture in vacuo to give an off white solid and the solid was diluted with methylene chloride and extracted with 1N HCl (20 mL), saturated sodium chloride solution (20 mL), dried ($Na_2SO_4$), and the solvent removed in vacuo to give an off-white solid. This material was recrystallized from ethyl acetate to give 5.6 g (34.7% yield) of 1-(2-fluoro-6-chlorobenzoyl)-2-methyl-2-[(4-methylphenyl)sulfonyl] hydrazine as a crystalline solid: mp 135–136° C.; $^1$H NMR ($CDCl_3$) δ 7.6–7.8 (m, 3H), 7.0–7.4 (m, 5H), 3.4 and 3.0 (singlets combined for 3H), 2.4 and 2.45 (singlets combined for 3H); $^{13}$C ($CDCl_3$) 160.2, 144.7, 133.6, 132.7, 132.6, 132.1, 131.9, 130.2, 129.6, 129.0, 128.7, 125.7, 114.6, 114.3, 37.7, 21.7. Anal. Calcd. For $C_{15}H_{14}ClFN_2O_3S$: C, 50.49; H, 3.95; N, 7.85. Found: C, 50.55; H, 3.89: N. 7.81.

C. N-(4-methylbenzenesulfonyl)-N-methyl-(2-fluoro-6-chlorobenz)hydrazonoyl chloride Into a 250 mL one necked round bottom flask equipped with magnetic stirrer and condenser, under an atmosphere of nitrogen, was added 1-(2-fluoro-6-chlorobenzoyl)-2-methyl-2-[(4-methylphenyl)sulfonyl]hydrazine (5.0 g. 14.0 mmol), ethylene dichloride (50 mL), and phosphorus pentachloride (3.2 g, 21.6 mmol). The mixture was heated to reflux and was maintained at that temperature for approximately 30 min. The progress of the reaction was monitored by TLC using 50/50 ethyl acetate/hexanes (starting material Rf=0.55; product Rf=0.70). The solvent was removed in vacuo and the residue dissolved in methylene chloride (100 mL) and carefully diluted with water. The organic phase was washed with water, brine, dried ($Na_2SO_4$) and the solvent removed in vacuo to give a yellow oil which solidified upon cooling. The solids were slurried in hexane/ethyl acetate (70/30) and removed via filtration to give 4.5 g (87% yield) of N-(4-methylbenzenesulfonyl)-N-methyl-(2-fluoro-6-chlorobenz)hydrazonoyl chloride. MP 98–99° C. ; $^1$H NMR ($CDCl_3$) δ 7.8 (d, 2H), 7.2–7.5 (m, 4H), 7.1 (m, H); 3.1 (s, 3H), 2.5 (s, 3H); $^{13}$C NMR ($CDCl_3$) 161.6, 158.5, 144.6, 140.7, 133.6, 132.1, 131.9, 131.1, 129.5, 125.6, 125.5, 114.7, 114.4, 38.1, 21.6. Anal. Calcd. for $C_{15}H_{13}Cl_2FN_2O_2S$: C, 48.01; H, 3.49; N, 7.47. Found: C, 48.10; H, 3.49; N, 7.47.

EXAMPLE 11

3-(2-chloro-6-fluorophenyl)-5-(3,4,5-trichlorothien-2-yl)-1-methyl[1,2,4]triazole (Compound 2)

Into a 50 mL necked flask equipped with a magnetic stirrer and thermometer, under an atmosphere of nitrogen, was added N-(4-methylbenzenesulfonyl)-N-methyl-(2-fluoro-6-chlorobenz)hydrazonoyl chloride (Example 10) (1.4 g, 3.73mmol), 2-cyano-3,4,5-trichlorothiophene (0.83 g, 3.92 mmol), aluminum chloride (0.53 g, 4.0 mmol), and o-dichlorobenzene (10 mL). The flask containing the reaction mixture was immersed into a preheated oil bath maintained at 120° C. Within 8 minutes the temperature of the reaction mixture rose to 109° C. and heating was continued for an additional 30 min. The flask was removed from the oil bath. When the stirred reaction mixture reached approximately 80° C. and was poured into a solution (10 g of sodium hydroxide with 10 mL of ice) with rapid stirring and was then added to methylene chloride (50 mL) for extraction. The organic phase was washed with water (25 mL), brine, dried ($Na_2SO_4$), and the solvent removed in vacuo. The o-dichlorobenzene was removed from the residue via kugelrohr distillation to give a residue which was dissolved in ether (20 mL), stirred with activated carbon at RT, filtered, and the solvent was removed in vacuo from the filtrate. The solids were recrystallized from ethyl acetate to give 0.9 g (60.8% yield) of 3-(2-chloro-6-fluorophenyl)-5-(3,4,5-trichlorothien-2-yl)-1-methyl[1,2,4]triazole as a crystalline solid: >97% pure by HPLC analysis; $^1$H NMR ($CDCl_3$) 37.2–7.4 (m, 2H), 7.0–7.4 (m, 1H), 4.0 (s, 3H).

EXAMPLE 12

This Example shows preparation of the benzhydrazonoyl chloride of formula (14c):

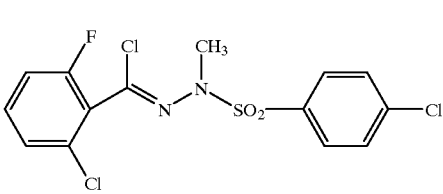

(14c)

A. 2-methyl-2-[(4-chlorophenyl)sulfonyl] hydrazine

Into a 100 mL three necked round bottom flask equipped with a mechanical stirrer, thermometer, and dropping funnel under an atmosphere of nitrogen was added THF (25 mL), methylhydrazine (2.53 g, 2.92 mL, 55 mmol), and triethylamine (4.35 g, 43 mmol). The temperature of the mixture was lowered to approximately 5° C. and crude 4-chlorophenylsulfonyl chloride (10.5 g, 50 mmol, contained 4-chlorophenyl sulfonic acid) dissolved in 25 mL of THF was added dropwise at a rate such that the temperature did not rise over 10° C. The cooling bath was removed and the mixture was allowed to warm to stir overnight at RT. Ether (100 mL was added to the reaction mixture and the resulting slurry was washed with water (50 mL), brine (50 mL), dried (Na$_2$SO$_4$), and the solvent was removed in vacuo to give 5.4 g (49% yield) of 2-methyl-2-[(4-chlorophenyl)sulfonyl] hydrazine. $^1$H NMR (CDCl$_3$) δ 7.8 (d, 2H), 7.6 (d, 2H), 3.6 (s, b, 2H), 2.9 (s, 3H).

B. 1-(2-fluoro-6-chlorobenzoyl)-2-methyl-2-[(4-chlorophenyl)sulfonyl] hydrazine

Into a 100 mL three necked round bottom flask equipped with a magnetic stirrer and condenser, under an atmosphere of nitrogen, was added 2-methyl-2-[(4-chlorophenyl)sulfonyl] hydrazine (5.4 g, 24.5 mmol), pyridine (1.93 g, 1.98 mL, 24.5 mmol), 4-dimethylaminopyridine (0.15 g, 1.2 mmol), and acetonitrile (50 mL). The mixture was cooled to 10° C. and 2-fluoro-6-chlorobenzoyl chloride (4.65 g, 23.4 mmol) was added dropwise at a rate such that the temperature did not rise above 10° C. The mixture was allowed to stir at RT overnight. The solvent was removed from the reaction mixture in vacuo to give an off white solid and the solid was diluted with methylene chloride and extracted with 1N HCl (20 mL), saturated sodium bicarbonate (20 mL), dried (Na$_2$SO$_4$), and the solvent removed in vacuo to give 1-(2-fluoro-6-chlorobenzoyl)-2-methyl-2-[(4-chlorophenyl)sulfonyl] hydrazine as a yellow oil which was used without purification.

C. N-(4-chlorophenylsulfonyl)-N-methyl-(2-fluoro-6-chlorobenz)hydrazonoyl chloride Into a 250 mL one necked round bottom flask equipped with magnetic stirrer and condenser, under an atmosphere of nitrogen, was added 1-(2-fluoro-6-chlorobenzoyl)-2-methyl-2-(4-chlorophenylsulfonyl) hydrazine (7.3 g, 16.8 mmol, 87% pure by HPLC), ethylene dichloride (50 mL), and phosphorus pentachloride (6.03 g, 28.9 mmol). The mixture was heated to reflux and was maintained at that temperature for approximate 30 min. The solvent was removed in vacuo and the residue dissolved in methylene chloride (100 mL) and carefully diluted with water. The organic phase was washed with water, brine, dried (Na$_2$SO$_4$) and the solvent removed in vacuo to give a yellow oil which was dissolved in hot ethyl acetate to which was added hexanes to the cloud point and upon cooling with scratching solids were formed. The solids were recrystallized from hexane/ethyl acetate (70/30) and seeded to give 2.7 g (40.9% yield) of N-(4-chlorophenylsulfonyl)-N-methyl-(2-fluoro-6-chlorobenz)hydrazonoyl chloride. MP 100–101° C.; $^1$H NMR (CDCl$_3$) δ 7.8 (d, 2H), 7.2–7.5 (m, 4H), 7.1 (m, H), 3.1 (s, 3H), 2.5 (s, 3H). Anal. Calcd. for C$_{14}$H$_{10}$Cl$_3$FN$_2$O$_2$S: C, 42.50; H, 2.55; N, 7.08. Found: C, 42.56; H, 2.47; N, 6.99.

EXAMPLE 13

3-(2-chloro-6-fluorophenyl)-5-(3,4,5-trichlorothien-2-yl)-1-methyl[1,2,4]triazole (Compound 2)

Into a 50 mL necked flask equipped with a magnetic stirrer and thermometer, under an atmosphere of nitrogen, was added N-(4-chlorophenylsulfonyl)-N-methyl-(2-fluoro-6-chlorobenz)-hydrazonoyl chloride (Preparation 4) (2.7 g, 6.8 mmol), 2-cyano-3,4,5-trichlorothiophene (1.44 g, 6.8 mmol), aluminum chloride (1.18 g, 8.9 mmol), and o-dichlorobenzene (20 mL). The flask containing the reaction mixture was immersed into a preheated oil bath maintained at 120° C. Within 8 minutes the temperature of the reaction mixture rose to 109° C. and heating was continued for an additional 50 min. The flask was removed from the oil bath. When the stirred reaction mixture reached approximately 80° C. and was poured into a solution 20 g of sodium hydroxide with 20 mL of ice) with rapid stirring and was then added to methylene chloride (100 mL) for extraction. The organic phase was washed with water, brine, dried (Na$_2$SO$_4$), and the solvent removed in vacuo. The o-dichlorobenzene was removed from the residue via kugelrohr distillation to give a residue which was dissolved in ether (50 mL), stirred with activated carbon at RT, filtered, and the solvent was removed in vacuo from the filtrate. The resulting off white solids were recrystallized to give 1.8 g (26.6% yield) of 3-(2-chloro-6-fluorophenyl)-5-(3,4,5-trichlorothien-2-yl)-1-methyl[1,2,4]triazole as a crystalline solid: >98% pure by HPLC analysis.

EXAMPLE 14

This Example shows preparation of the benzhydrazonoyl chloride of formula (14d):

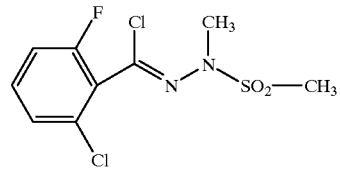

(14d)

A. 2-Methyl-2-methanesulfonyl hydrazine

Into a 250 mL three necked round bottom flask equipped with a mechanical stirrer, thermometer, and dropping funnel under an atmosphere of nitrogen was added THF (100 mL), methyl hydrazine (5.07 g, 5.85 mL, 110 mmol), and triethylamine (11.1 g, 15.3 mL, 110 mmol). The temperature of the mixture was lowered to approximately 5° C. and methanesulfonyl chloride (11.4 g, 7.73 mL, 100 mmol) was added dropwise at a rate such that the temperature did not rise above 10° C. The cooling bath was removed and the mixture was allowed to warm to RT and was stirred over night. Ether (100 mL) was added to the reaction mixture and washed with water (50 mL), brine (50 mL), dried (Na$_2$SO$_4$), and the solvent was removed in vacuo to give 2.4 g (19.3% yield) of 2-methyl-2-methanesulfonyl hydrazine. $^1$H NMR (CDCl$_3$) δ 3.8 (s, b, 2H), 2.95 (s, 3H), 2.9 (s, 3H).

B. 1-(2-fluoro-6-chlorobenzoyl)-2-methyl-2-methanesulfonyl hydrazine

Into a 50-mL was added 2-methyl-2-methanesulfonyl hydrazine (2.4 g, 19.3 mmol), pyridine (1.5 g, 1.55 mL, 19.3 mmol), and acetonitrile (20 mL), under an atmosphere of nitrogen. The mixture was cooled to approximately 0° C. and 2-chloro-6-fluorobenzoyl chloride (3.77 g, 19.3 mmol) was added dropwise. The mixture was allowed to warm to RT and to stir for approximately 3 hr with monitoring by TLC using 50/50 ethyl acetate/hexanes (Rf=0.7 for 2-chloro-6-fluorobenzoyl chloride and Rf=0.44 for product). The solvent was removed from the reaction mixture in vacuo, the residue was diluted with methylene chloride, and extracted with 1N hydrochloric acid (10 mL), saturated sodium bicarbonate, dried (MgSO$_4$), and the solvent removed in vacuo to give 4.6 g of a semi-solid. This material was recrystallized from ethyl acetate to give 1.8 g (33.3% yield) of 1-(2-fluoro-6-chlorobenzoyl)-2-methyl 2-methanesulfonyl hydrazine as a crystalline solid. MP 135–136° C.; $^1$H NMR (CDCl$_3$) δ 7.8 (s, b, 1H), 7.2–7.4 (m, 3H), 3.4 (s, 3H), 3.15 (s, 3H). Anal. Calcd. for C$_9$H$_{10}$ClFN$_2$O$_3$S: C, 38.51; H, 3.59; N, 9.98. Found: C, 38.28, H, 3.41; N. 9.48.

C. N-methanesulfonyl-N-methyl-(2-fluoro-6-chlorobenz) hydrazonoyl chloride

Into a 250 mL one necked round bottom flask equipped with magnetic stirrer and condenser, under an atmosphere of nitrogen, was added 1-(2-fluoro-6-chlorobenzoyl)-2-methyl-2-methanesulfonyl hydrazine (1.6 g, 7.12 mmol), ethylene dichloride (25 mL), and phosphorus pentachloride (2.2 g, 10.7 mmol). The mixture was heated to reflux and was maintained at that temperature for approximate 30 min. Theprogress of the reaction was monitored by TLC using 50/50 ethyl acetate/hexanes (starting material Rf=0.44; product Rf=0.60. The solvent was removed in vacuo and the residue dissolved in methylene chloride (50 mL) and carefully diluted with water. The organic phase was washed with water (2×50 mL), brine (50 mL), dried (Na$_2$SO$_4$) and the solvent removed in vacuo to give a colorless oil which solidified upon cooling. The solids were recrystallized from hexanes/ethyl acetate (70/30) to give 1.2 g (56.6% yield) of N-methanesulfonyl-N-methyl-(2-fluoro-6-chlorobenz) hydrazonoyl chloride. MP 83–85° C. ; 93% pure by HPLC analysis: 1H NMR (CDCl$_3$) δ 7.8 (d, 2H), 7.0–7.4 (m, 3H), 3.45 and 3.35 (singlets adding to 3H), 3.15 and 3.05 (singlets adding to 3H).

EXAMPLE 15

3-(2-chloro-6-fluorophenyl)-5-(3,4,5-trichlorothien-2-yl)-1-methyl[1,2,4]triazole (Compound 2)

Into a 50 mL necked flask equipped with a magnetic stirrer and thermometer, under an atmosphere of nitrogen, was added N-methanesulfonyl-N-methyl-(2-fluoro-6-chlorobenz)hydrazonoyl chloride (Example 14)(1.0 g, 3.3 mmol), 2-cyano-3,4,5-trichlorothiophene (0.78 g, 3.7 mmol), aluminum chloride (0.49 g, 3.7 mmol), and o-dichlorobenzene (10 mL). The flask containing the reaction mixture was immersed into a preheated oil bath maintained at 120° C. Within 10 minutes the temperature of the reaction mixture rose to 111° C. and heating was continued for an additional 90 min. GC analysis indicated that the conversion of the reaction was approximately 66%. The flask was removed from the oil bath. When the stirred reaction mixture reached approximately 90° C. and was poured into a solution (10 g of sodium hydroxide with 10 mL of ice) with rapid stirring and was then added to methylene chloride (50 mL) for extraction. The organic phase was washed with water (25 mL), brine, dried (Na$_2$SO$_4$), and the solvent removed in vacuo. The o-dichlorobenzene was removed from the residue via kugelrohr distillation to give a residue which was dissolved in ether (20 mL), stirred with activated carbon at RT, filtered, and the solvent was removed in vacuo from the filtrate to give 0.4 g of 3-(2-chloro-6-fluorophenyl)-5-(3,4,5-trichlorothien-2-yl)-1-methyl[1,2,4] triazole contaminated with 3,4,5-trichloro-2-cyanothiophene.

Compounds of the invention can be modified using conventional processes to provide other compounds of the invention, as illustrated in Examples 16 and 17.

EXAMPLE 16

3-(2,6-dichlorophenyl)-5-(5-bromo-3,4-dichlorothien-2-yl)-1-methyl[1,2,4]triazole (Compound 46)

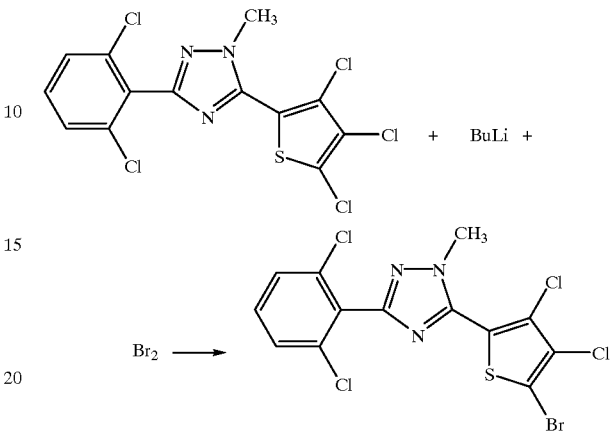

n-Butyllithium (2.5 mmol) was slowly added to a solution of 3-(2,6-dichlorophenyl)-5-(3,4,5-trichlorothien-2-yl)-1-methyl[1,2,4]triazole (325 mg, 1.0 mmol) in THF at −78° C., and the mixture was stirred one hour. Bromine (3.0 mmol) was added and the reaction stirred two hours, then diluted with water, extracted with ether, washed with brine, and dried over magnesium sulfate. The product was concentrated to 620 mg of dark oil. This was chromatographed (SiO$_2$, 10% EtOAc-Hex) to give 79 mg of the title product as a pink solid. MP 197–199° C.

EXAMPLE 17

3-(2,6-dichlorophenyl)-5-(5-bromothien-2-yl)-1-methyl[1,2,4]triazole (Compound 47)

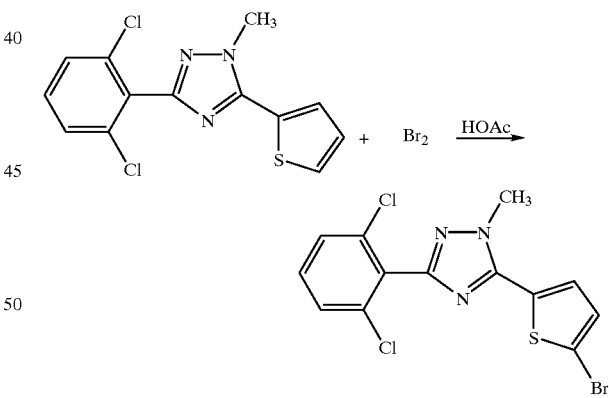

3-(2,6-dichlorophenyl)-5-(thien-2-yl)-1-methyl-[1,2,4] triazole (75 mg, 0.242 mmol) and bromine (39 mg, 0.242 mmol) were combined in glacial acetic acid (3mL) and the mixture was stirred overnight at room temperature, then heated to 95° C. for five hours. The reaction mixture was poured into a saturated sodium bicarbonate solution, extracted with ether, and dried over magnesium sulfate. Chromatography (SiO$_2$, 25% Hex-CH$_2$Cl$_2$) delivered the title product as a waxy white solid. MP 130–132° C.

Phytologically acceptable acid addition salts of the compounds of formula (1) are also within the scope of the invention. For example, boron tetrafluoride, hydrogen chloride, hydrogen bromide, hydrogen iodide, hydrogen sulfate, or organic acid salts may be used.

The compounds identified in the following Table 1 were pared and tested.

TABLE I

| cmpd no. | R¹ | R¹' | R² | Q¹ | mp °C. | CA† | TSSM‡ | WF* |
|---|---|---|---|---|---|---|---|---|
| 1 | Cl | F | $CH_3$ | 5-chloro-2-methylthiophene | 112–113 | A | C | E |
| 2 | Cl | F | $CH_3$ | 3,4,5-trichloro-2-methylthiophene | 127–128 | A | A | B |
| 3 | Cl | F | $CH_3$ | 5-(oxazol-4-yl)-2-methylthiophene | 145–147 | G | A | |
| 4 | F | F | $CH_3$ | 2-methylfuran | oil | F | | |
| 5 | F | F | $CH_3$ | 3,4,5-trichloro-2-methylthiophene | 137–138 | A | F | B |
| 6 | F | F | $CH_3$ | 3-chloro-2-methylbenzothiophene | 104–106 | C | | E |
| 7 | F | F | $CH_3$ | 3-chloro-2-methylthiophene | 60–61 | A | A | C |
| 8 | F | F | $CH_3$ | 3-chloro-4-(isopropylsulfonyl)-2-methylthiophene | 176–177 | F | | |
| 9 | F | F | $CH_3$ | 5-nitro-2-methylfuran | 172–173 | F | | |

TABLE I-continued
| 10 | F | F | CH$_3$ | 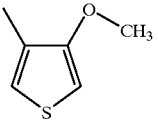 | oil | A | A | C |
| --- | --- | --- | --- | --- | --- | --- | --- | --- |
| 11 | F | F | CH$_3$ | 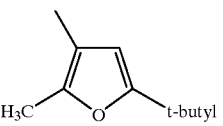 | 76–78 | F | | |
| 12 | F | F | CH$_3$ | 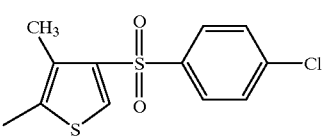 | 183–185 | G | A | G |
| 13 | F | F | CH$_3$ | 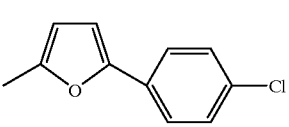 | 171–173 | B | A | |
| 14 | F | F | CH$_3$ | 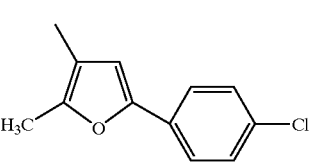 | 146–148 | D | | |
| 15 | Cl | F | CH$_3$ | 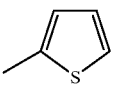 | 109–111 | A | F | D |
| 16 | F | F | CH$_3$ | 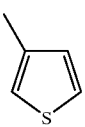 | 101–102 | A | A | G |
| 17 | F | F | CH$_3$ | 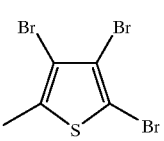 | 153–154 | A | A | F |
| 18 | Cl | F | CH$_3$ | 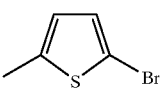 | 123–124 | A | C | D |
| 19 | F | F | CH$_3$ | 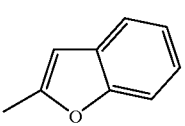 | 98–100 | A | | |
| 20 | Cl | F | CH$_3$ | 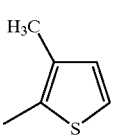 | 80–82 | A | D | A |

TABLE I-continued

| | | | | | | | | |
|---|---|---|---|---|---|---|---|---|
| 21 | Cl | F | CH₃ | 4-methyl-2-nitrothiophene | 113–115 | C | A | G |
| 22 | Cl | F | CH₃ | 5-methyl-2-nitrothiophene | 129–130 | G | A | F |
| 23 | F | F | CH₃ | 5-methyl-2-(4-chlorophenyl)thiophene | 127–129 | F | G | D |
| 24 | F | F | CH₃ | 5-methyl-3-(4-methoxyphenyl)thiophene | 106–108 | F | B | F |
| 25 | F | F | CH₃ | 2,5-dimethyl-3-phenylthiophene | 135–136 | F | A | G |
| 26 | F | F | CH₃ | 2,3-dibromo-5-methylthiophene | 136–138 | A | C | F |
| 27 | F | F | CH₃ | 5-methyl-2-(3,5-dichlorophenoxy)furan | oil | E | | |
| 28 | F | F | CH₃ | 3-bromo-5-methyl-2-(3-chlorophenoxy)thiophene | 142–144 | F | A | F |
| 29 | F | F | CH₃ | 5-methyl-2-(4-methoxyphenyl)thiophene | 100–101 | A | B | F |
| 30 | F | F | CH₃ | 2-trifluoromethyl-3-methyl-5-(4-chlorophenyl)furan | 159–161 | G | | |

TABLE I-continued
| | | | | | | | |
|---|---|---|---|---|---|---|---|
| 31 | F | F | CH₃ | 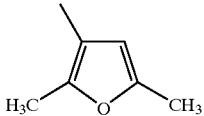 | oil | C | |
| 32 | F | F | CH₃ | 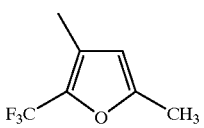 | 53–55 | A | |
| 33 | F | F | CH₃ | 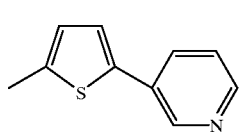 | 169–170 | F | |
| 34 | Cl | F | CH₃ |  | 100–101 | A | G |
| 35 | F | F | CH₃ | 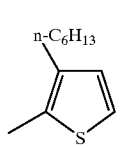 | oil | D | |
| 36 | F | F | CH₃ | 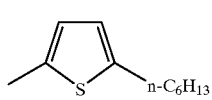 | oil | F | |
| 37 | Cl | F | CH₃ | 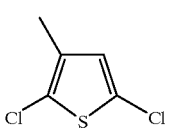 | oil | A | E |
| 38 | Cl | F | CH₃ | 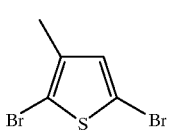 | 138–139 | A | |
| 39 | Cl | F | CH₃ | 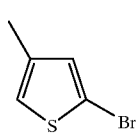 | 83–84 | A | B |
| 40 | F | F | CH₃ | 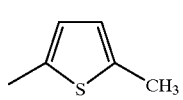 | 97–99 | D | |
| 41 | F | F | CH₃ | 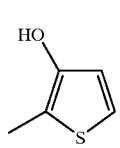 | 146–147 | G | |

TABLE I-continued
| 42 | F | F | CH₃ | 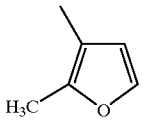 | oil | A |
| 43 | F | F | CH₃ | 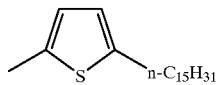 | 63–64 | F |
| 44 | F | F | CH₃ | 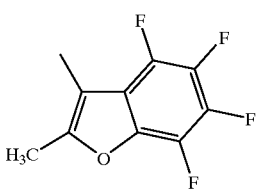 | 115–117 | F |
| 45 | Cl | Cl | CH₃ | 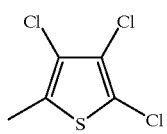 | 151–152 | A |
| 46 | Cl | Cl | CH₃ | 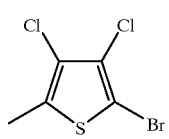 | 197–199 | A |
| 47 | Cl | Cl | CH₃ | 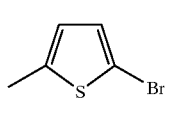 | 130–132 | A |
| 48 | Cl | Cl | CH₃ | 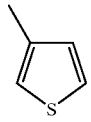 | oil | A |
| 49 | Cl | Cl | CH₃ | 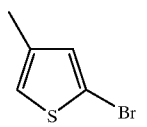 | yellow oil | A |
| 50 | Cl | Cl | CH₃ | 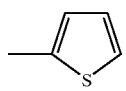 | 161–163 | A |
| 51 | F | F | CH₃ | 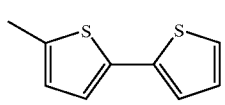 | 116–118 | G |
| 52 | F | F | CH₃ | 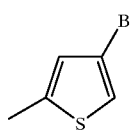 | 153–155 | D |
| 53 | F | F | CH₃ | 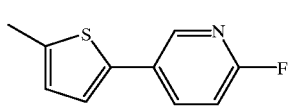 | 147–148 | G |

TABLE I-continued

| 54 | F | F | CH₃ | (2-methyl-7-ethoxybenzofuran) | 88–90 | F | |
| 55 | F | F | CH₃ | (3-methyl-2,4,5-tribromothiophene / 2:1 Br to Cl) | oil | G | |
| 56 | F | F | CH₃ | (2-chloro-3-methoxy-4-methylthiophene) | 83–85 | B | |
| 57 | F | F | CH₃ | (2-methyl-5-methoxythiophene) | 125–126 | A | G |
| 58 | Cl | F | CH₃ | (3-bromo-2-methylthiophene) | 99–100 | B | |
| 59 | F | F | CH₃ | (5-chloro-2-methylbenzofuran) | 150–152 | D | |
| 60 | Cl | F | CH₃ | (2-methyl-5-methylthiothiophene) | oil | B | |
| 61 | F | F | CH₃ | (3-bromo-2-methylthiophene) | 98–99 | A | |
| 62 | Cl | F | CH₂Cl | (2-methyl-3,4,5-trichlorothiophene) | 105–106 | A | |
| 63 | F | F | CH₃ | (3-(4-chlorophenyl)-4-methylthiophene) | oil | G | |
| 64 | F | F | CH₃ | (5-methyl-2-(2-pyridyl)thiophene) | 144–146 | G | |

TABLE I-continued
| 65 | Cl | F | CHCl₂ | 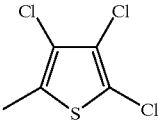 | 114–115 | F |
| 66 | F | F | CH₃ | 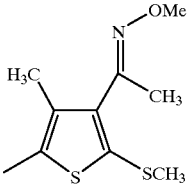 | oil | A |
| 67 | Cl | F | CH₃ | 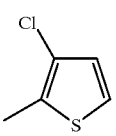 | 87–88 | A |
| 68 | Cl | F | CH₃ | 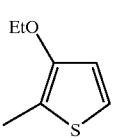 | 111–113 | G |
| 69 | F | F | CH₃ | 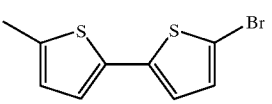 | 127–129 | F |
| 70 | F | F | CH₃ | 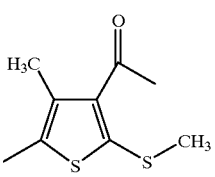 | oil | F |
| 71 | Cl | F | CH₃ | 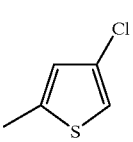 | 130–132 | A |
| 72 | F | F | CH₃ | 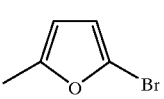 | oil | F |
| 73 | F | F | CH₃ | 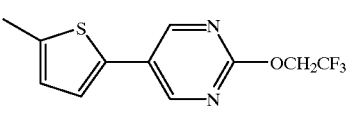 | 177 | F |
| 74 | Cl | F | CH₃ | 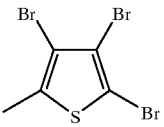 | 206–208 | A |
| 75 | Cl | F | CH₂CH₃ | 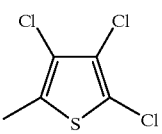 | 83–84 | A |

TABLE I-continued
| | | | | | | |
|---|---|---|---|---|---|---|
| 76 | F | F | CH₃ | 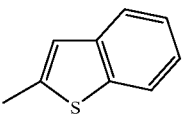 | 145–147 | C |
| 77 | F | F | CH₃ | 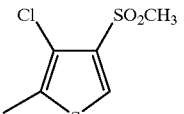 | 141–142 | F |
| 78 | F | F | CH₃ | 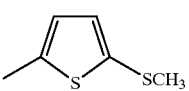 | oil | B |
| 79 | F | F | CH₃ | 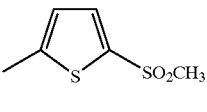 | 157–158 | F |
| 80 | Cl | F | CH₃ | 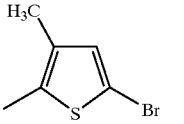 | 117–118 | A |
| 81 | Cl | F | CH₂CH₂CH₃ | 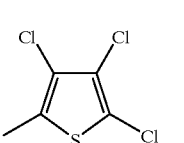 | 116–117 | D |
| 82 | Cl | F | CH₂CN | 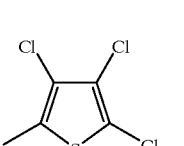 | oil | F |
| 83 | Cl | F | CHClF | 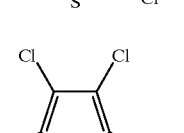 | oil | D |
| 84 | Cl | F | CH₂SCH₃ | 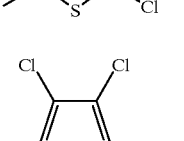 | oil | F |
| 85 | Cl | F | CH₂OCH₃ | 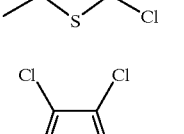 | oil | A |
| 86 | Cl | F | CH₂SCH₃ | 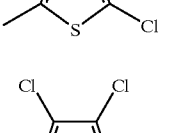 | oil | A |

TABLE I-continued
| | | | | | | |
|---|---|---|---|---|---|---|
| 87 | F | F | CH₃ | 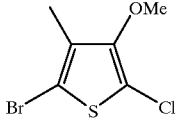 | oil | E |
| 88 | F | F | CH₃ | 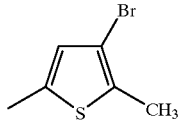 | 122 | F |
| 89 | Cl | F | CH₃ | 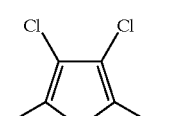 | 101.5–102 | E |
| 90 | Cl | F | CH₃ | 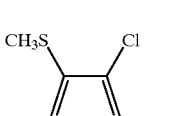 | 115–116.5 | A |
| 91 | F | F | CH₃ | 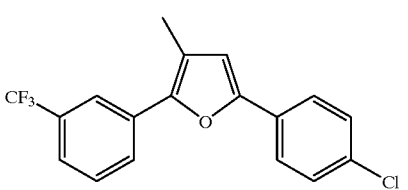 | 157–159 | D |
| 92 | Cl | F | CH₃ | 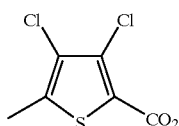 | 109.5–112 | B |
| 93 | Cl | F | CH₃ | 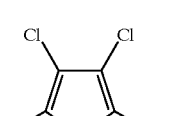 | 267–270 dec | F |
| 94 | Cl | F | CH₃ | 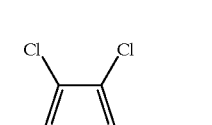 | 178–180 | F |
| 95 | Cl | F | CH₃ | 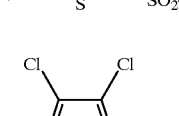 | 95–97 | B |
| 96 | Cl | F | CH₃ | 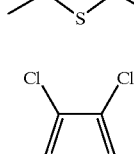 | 118–120 | A |

TABLE I-continued
| | | | | | | |
|---|---|---|---|---|---|---|
| 97 | Cl | F | CH$_3$ | 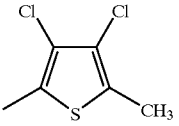 | 82–83.5 | B |
| 98 | Cl | F | CH$_2$SO$_2$CH$_3$ | 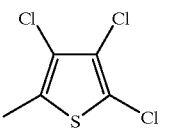 | 207–209 | F |
| 99 | Cl | F | CH$_2$F | 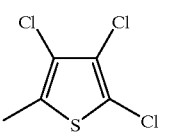 | oil | A |
| 100 | Cl | F | CH$_3$ | 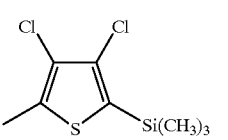 | 133–135 | B |
| 101 | Cl | F | CH$_3$ | 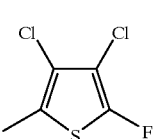 | 128–131 | A |
| 102 | Cl | F | CH$_3$ | 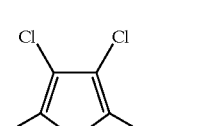 | 126–131 | B |
| 103 | Cl | F | CH$_3$ | 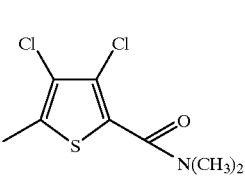 | 131–133 | C |
| 104 | Cl | F | CH$_3$ | 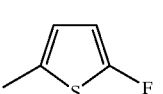 | 113–115 | A |
| 105 | Cl | F | CH$_3$ | 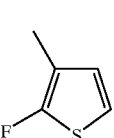 | 59–64 | A |
| 106 | Cl | F | CH$_3$ | 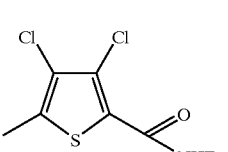 | 162.5–164 | F |
| 107 | Cl | F | CH$_3$ | 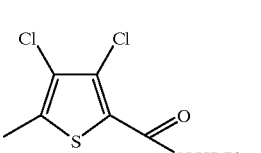 | oil | F |

TABLE I-continued
| | | | | | | |
|---|---|---|---|---|---|---|
| 108 | H | Cl | CH₃ | 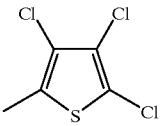 | 162–164 | C |
| 109 | Cl | F | CH₃ | 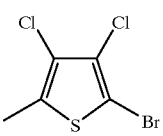 | 178–180 | A |
| 110 | Cl | F | CH₃ | 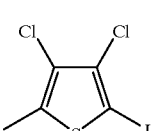 | 218–223 | A |
| 111 | Cl | Cl | CH₃ | 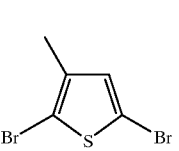 | oil | C |
| 112 | H | Cl | CH₃ | 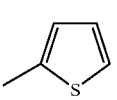 | oil | B |
| 113 | H | Cl | CH₃ | 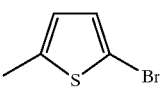 | oil | A |
| 114 | H | CF₃ | CH₃ | 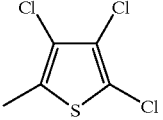 | 155–156 | F |
| 115 | Cl | F | CH₃ | 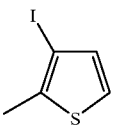 | 68–72 | A |
| 116 | Cl | F | CH₃ | 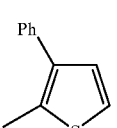 | 107–110 | F |
| 117 | Cl | F | CH₃ | 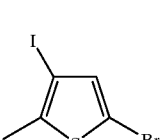 | 131–133 | B |
| 118 | Cl | F | CH₃ | 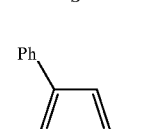 | oil | F |

TABLE I-continued
| | | | | | | |
|---|---|---|---|---|---|---|
| 119 | Cl | F | CH₃ | 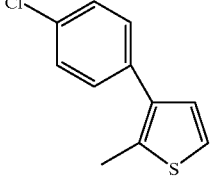 | oil | F |
| 120 | Cl | F | CH₃ | 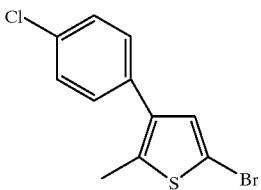 | oil | F |
| 121 | Cl | F | CH₃ | 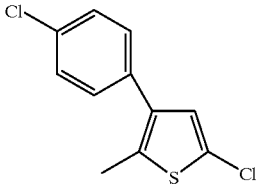 | oil | F |
| 122 | F | F | CH₃ | 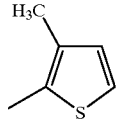 | 97–99 | B |
| 123 | F | F | CH₃ | 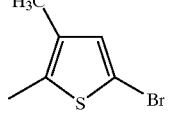 | 89–91 | C |
| 124 | Cl | F | CH₃ | 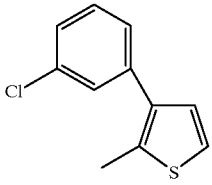 | oil | G |
| 125 | Cl | F | CH₃ | 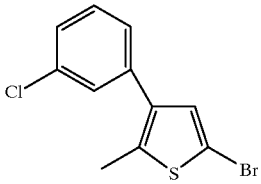 | oil | F |
| 126 | Cl | F | CH₃ | 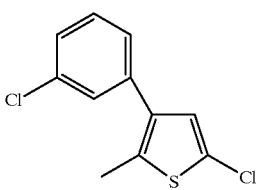 | oil | F |

TABLE I-continued
| 127 | Cl | Cl | CH₃ | 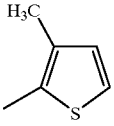 | | C |
| 128 | Cl | Cl | CH₃ | 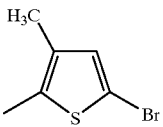 | | G |
| 129 | Cl | F | CH₃ | 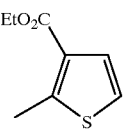 | oil | F |
| 130 | Cl | F | CH₃ | 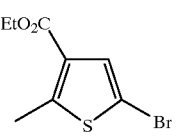 | 103–106 | F |
| 131 | Cl | F | CH₃ | 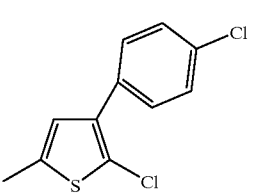 | 157–158 | F |
| 132 | Cl | F | CH₃ | 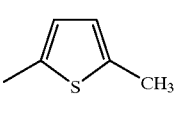 | 97–98 | A |
| 134 | Cl | F | CH₃ | 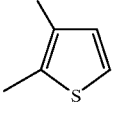 | 113–115 | G |
| 135 | Cl | Cl | CH₃ | 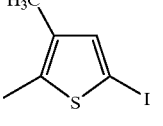 | | C |
| 136 | Cl | Cl | CH₃ | 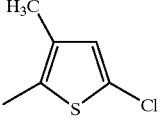 | | B |
| 137 | Cl | Cl | CH₃ | 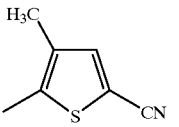 | | C |
| 138 | Cl | F | CH₃ | 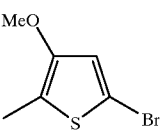 | 121–122 | F |

TABLE I-continued
| | | | | | | |
|---|---|---|---|---|---|---|
| 139 | Cl | F | CH₃ | 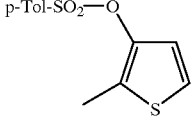 | 129–130 | G |
| 140 | Cl | F | CH₃ | 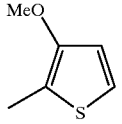 | oil | C |
| 141 | OMe | Cl | CH₃ | 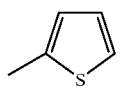 | oil | A |
| 142 | OMe | Cl | CH₃ | 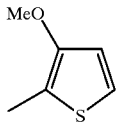 | 146–148 | F |
| 143 | Cl | F | CH₃ | 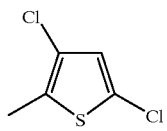 | 97–103 | A |
| 144 | F | F | CH₃ | 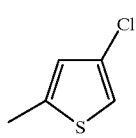 | 92–94 | A |
| 145 | F | F | CH₃ | 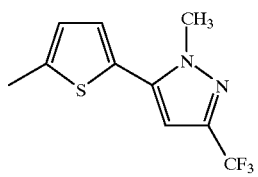 | 133–134 | F |
| 146 | Cl | F | CH₃ | 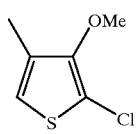 | | |
| 147 | Cl | Cl | CH₃ | 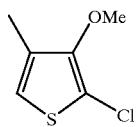 | | |
| 148 | Cl | F | CH₃ | 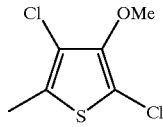 | | |

TABLE I-continued
| | | | | |
|---|---|---|---|---|
| 149 | Cl | F | CH$_3$ | 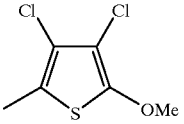 |
| 150 | Cl | F | CH$_3$ | 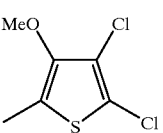 |
| 151 | Cl | F | CH$_3$ | 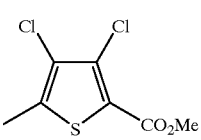 |
| 152 | Cl | F | CH$_3$ | 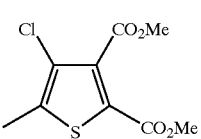 |
| 153 | Cl | F | CH$_3$ | 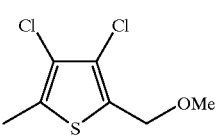 |
| 154 | Cl | F | CH$_3$ | 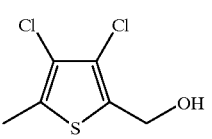 |
| 155 | Cl | F | CH$_3$ | 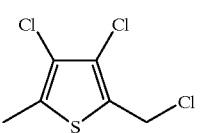 |
| 156 | Cl | F | CH$_3$ | 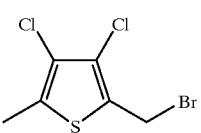 |
| 157 | OCH$_3$ | Cl | CH$_3$ | 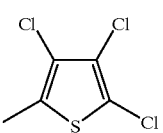 |
| 158 | OCH$_3$ | F | CH$_3$ | 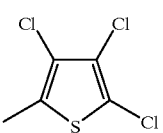 |
| 159 | CH$_3$ | Cl | CH$_3$ | 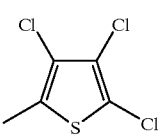 |

TABLE I-continued
| cmpd no. | Ar | R² | Q¹ | mp | CA† | TSSM‡ | WF* |
|---|---|---|---|---|---|---|---|
| 160 | CH₃  F  CH₃ | 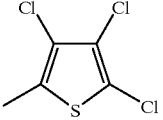 | | | | | |
| 161 | Cl  F  CH₃ | 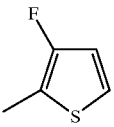 | | | | | |
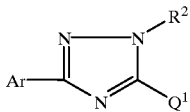
| cmpd no. | Ar | R² | Q¹ | mp | CA† | TSSM‡ | WF* |
|---|---|---|---|---|---|---|---|
| 162 | 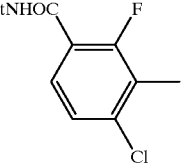 | CH₃ | 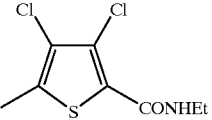 | 89–94 | G | | |
| 163 | 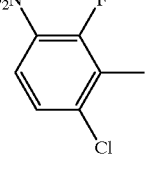 | CH₃ | 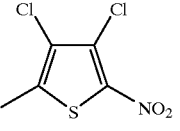 | 187–191 | | | |
| 164 | 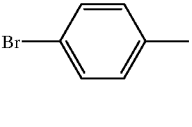 | CH₃ | 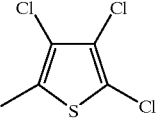 | 188–189 | F | | |
| 165 | 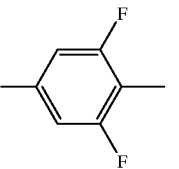 | CH₃ | 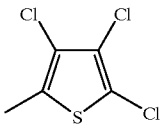 | | | | |
| 166 | 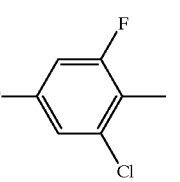 | CH₃ | 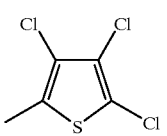 | | | | |
| 167 | 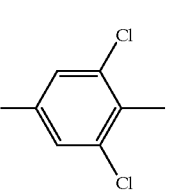 | CH₃ | 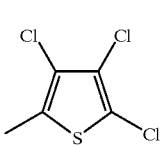 | | | | |

TABLE I-continued

| 168 | 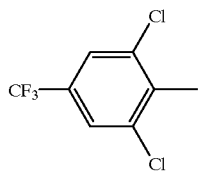 | 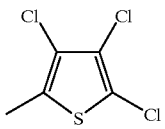 |

CA† refers to activity at 50 ppm against cotton aphid,
TSSM‡ refers to activity at 100 ppm against two-spotted spider mite, and
WF* refers to activity at 800 ppm against whitefly. The test procedures are described below.

In each case the rating scale is as follows

| % Control | Rating |
|---|---|
| 91–100 | A |
| 81–90 | B |
| 71–80 | C |
| 61–70 | D |
| 51–60 | E |
| less than 51 | F |
| inactive | G |

Insecticide and Miticide Utility

The compounds of the invention are also useful for the control of insects, mites, and aphids. Therefore, the present invention also is directed to a method for inhibiting an insect, mite, or aphid which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite, population. Generally an amount in the range from about 1 to about 1000 ppm active compound is used.

In a preferred embodiment, the present invention is directed to a method for inhibiting a mite or aphid which comprises applying to a plant an effective mite- or aphid-inactivating amount of a compound of formula (1).

Insecticidal test for cotton aphid (*Aphis gossypii*)

To prepare spray solutions, 2 mg of each test compound was dissolved into 2 mL of a 90:10 acetone:ethanol solvent. This 2 mL of chemical solution was added to 38 mL of water containing 0.05% Tween 20 surfactant to produce a 50 ppm spray solution.

Squash cotyledons were infested with cotton aphid (all life stages)16–20 hours prior to application of spray solution. The solution was sprayed on both sides of each infested squash cotyledon (0.5 mL×2 each side) with a sweeping action using a total of 2 mL of spray solution. The plants were allowed to air dry and held for 3 days in a controlled room at 26° C. and 40% RH after which time the test was graded. Grading was by actual count using a dissecting microscope and comparison of test counts to the untreated check. Results are given in Table 1 as percent control based on population reduction versus the untreated.

Insecticidal test for two-spotted spider mite (*Tetranychus urticae*)

Ovicide Method:

Ten adult female two-spotted spider mites were placed on eight 2.2 cm leaf discs of cotton leaf, allowed to oviposit over 24 hours, and thereafter removed. The leaf discs were immersed in 100 ppm test solutions for 3 seconds, then allowed to dry with sixteen discs left untreated as a negative control. Discs were placed on an agar substrate and held at 24° C. and 90% relative humidity for 6 days. Percent control based on the number of hatched larvae on treated discs and the number on untreated discs is reported in Table 1.

Evaluation of Tests Compounds on Sweetpotato Whitefly (*Bemisia tabacia*) Under Laboratory Conditions Sixteen mg of each test compound was dissolved by adding 5 ml of a 90:10 acetone:ethanol solvent mixture to the vial containing the sample compound. This solution was added to 15 ml of water containing 0.05% Tween 20 surfactant to produce 20 ml of an 800 ppm spray solution.

Five-week-old cotton plants reared in a greenhouse were stripped of all foliage except for the two uppermost true leaves that were greater than 5 cm in diameter. These plants were then placed into a laboratory colony of whiteflies for three days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (26° C. and 40% RH) for 21 days. Compound efficacy was evaluated by counting, under a dissecting microscope, the number of spent pupal cases per leaf. A spent pupal case represents a whitefly egg that has undergone full development to achieve adult status, thus indicating lack of control. Percent control based on reduction of spent pupal cases of a test compound compared to solution-only (no test compound) sprayed plants is reported in Table 1.

Seed Treatment Test vs. Cotton Aphid on Squash

Four-inch pots were filled two-thirds full with sieved soil mix (70 sand/30 pulverized soil). Compound was applied as a suspension to the center in 4 ml volume. Squash seed placed in the applied chemical zone was covered with soil mix 1 cm deep. The pots were irrigated and maintained in the greenhouse for ten days, at which time each plant had an expanded full leaf available for infestation. The plants were then infested with aphids. Four days later, aphid counts were made. Results are summarized in the following tables:

| Compound | Rate mg/pot | Mean | SD | % Ctrl. |
|---|---|---|---|---|
| Cotton aphid counts on Squash - cotyledon | | | | |
| Compound 2 | 12.8 | 7.0 | 6.2 | 93.3 |
| | 3.2 | 7.3 | 4.0 | 93.1 |
| | 0.8 | 48.0 | 42.1 | 54.4 |
| Compound 45 | 12.8 | 80.0 | 37.7 | 24.0 |
| | 3.2 | 50.3 | 14.8 | 52.3 |
| | 0.8 | 165.5 | 8.6 | 0 |
| Imidacloprid | 0.8 | 0 | 0 | 100 |
| (control) | 0.2 | 0 | 0 | 100 |
| | 0.05 | 2.5 | 3.5 | 97.6 |
| Check | 0 | 105.3 | 45.8 | 0 |
| Cotton aphid counts on Squash - 1$^{st}$ True Leaf | | | | |
| Compound 2 | 12.8 | 3.3 | 2.6 | 96.1 |
| | 3.2 | 3.5 | 2.4 | 95.9 |
| | 0.8 | 12.0 | 14.2 | 85.8 |
| Compound 45 | 12.8 | 8.3 | 5.1 | 90.2 |
| | 3.2 | 18.8 | 12.5 | 77.8 |
| | 0.8 | 40.8 | 18.9 | 51.7 |
| Imidacloprid | 0.8 | 0.0 | 0.0 | 100.0 |
| (control) | 0.2 | 9.8 | 6.5 | 88.4 |
| | 0.05 | 35.0 | 21.2 | 58.5 |
| Check | 0 | 84.4 | 53.2 | 0 |

In addition to being effective against mites, aphids, and insects when applied to foliage, compounds of formula (1) have exhibited systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (1).

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic.portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from-10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. 0.75 Emulsifiable Concentrate | |
|---|---|
| Compound of formula (1) | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |

| B. 1.5 Emulsifiable Concentrate | |
|---|---|
| Compound of formula (1) | 18.50% |
| "TOXIMUL D" | 2.50% |
| "TOXIMUL H" | 2.50% |
| "EXXON 200" | 76.50% |

| C. 1.0 Emulsifiable Concentrate | |
|---|---|
| Compound of formula (1) | 12.5% |
| N-methylpyrrolidone | 25.00% |
| "TOXIMUL D" | 2.50% |
| "TOXIMUL H" | 2.50% |
| "EXXON 200" | 57.50% |

| D. 1.0 Aqueous Suspension | |
|---|---|
| Compound of formula (1) | 12.00% |
| "PLURONIC P-103" (block copolymer of propylene oxide and ethylene oxide, surfactant) | 1.50% |
| "PROXEL GXL" (bio~ide/preservative) | .05% |
| "AF-100" (silicon based antifoam agent) | .20% |
| "REAX 88B" (lignostilfonate dispersing agent) | 1.00% |
| propylene glycol | 10.00% |
| veegum | .75% |
| xanthan | .25% |
| water | 74.25% |

| E. 1.0 Aqueous Suspension | |
|---|---|
| Compound of formula (1) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |

| F. 1.0 Aqueous Suspension | |
|---|---|
| Compound of formula (1) | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |

| G. Wettable Powder | |
|---|---|
| Compound of formula (1) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |

| H. 1.0 Aqueous Suspension | |
|---|---|
| Compound of formula (1) | 12.40% |
| "TERGITOL 158-7" | 5.00% |
| "ZEOSYL 200" | 1.0% |
| "AF-1G0" | 0.20% |
| "POLYFON H" | 0.50% |
| 2% xanthan solution | 10.00% |
| tap water | 70.90% |

| I. 1.0 Emulsifiable Concentrate | |
|---|---|
| Compound of formula (1) | 12.40% |
| "TOXIMUL D" | 2.50% |
| "TOXIMUL H" | 2.50% |
| "EXXON 200" | 82.60% |

| J. Wettable Powder | |
|---|---|
| Compound of formula (1) | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |

| K. 0.5 Emulsifiable Concentrate | |
|---|---|
| Compound of formula (1) | 6.19% |
| "TOXIMUL H" | 3.60% |
| "TOXIMUL D" | 0.40% |
| "EXXON 200" | 89.81% |

| L. Emulsifiable Concentrate | |
|---|---|
| Compound of formula (1) | 5 to 48 |
| surfactant or surfactant blend | 2 to 20% |
| Aromatic Solvent or Mixture | 55 to 75% |

We claim:

1. A compound of the formula (6)

$$\text{(6)}$$

[structure: 2,6-difluorophenyl group attached to C(=NH$_2$I)(S-R$^{11}$)]

wherein R$^{11}$ is lower alkyl.

* * * * *